United States Patent [19]
Cohen et al.

[11] Patent Number: 5,736,146
[45] Date of Patent: Apr. 7, 1998

[54] CONJUGATES OF POORLY IMMUNOGENIC ANTIGENS AND SYNTHETIC PEPTIDE CARRIERS AND VACCINES COMPRISING THEM

[75] Inventors: Irun R. Cohen; Matityahu Fridkin, both of Rehovot; Stephanie Konen-Waisman, Tel Aviv, all of Israel

[73] Assignee: Yeda Research and Development Co. Ltd., Israel

[21] Appl. No.: 379,613

[22] PCT Filed: Jul. 28, 1993

[86] PCT No.: PCT/US93/07096

§ 371 Date: Feb. 22, 1995

§ 102(e) Date: Feb. 22, 1995

[87] PCT Pub. No.: WO94/03208

PCT Pub. Date: Feb. 17, 1994

[30] Foreign Application Priority Data

Jul. 30, 1992 [IL] Israel ............................ 102687

[51] Int. Cl.[6] ................. A61K 39/385; A61K 39/09; A61K 39/112
[52] U.S. Cl. .................... 424/194.11; 424/184.1; 424/185.1; 424/190.1; 424/193.1; 424/194.1; 424/197.11; 424/258.1; 424/278.1
[58] Field of Search ............... 424/184.1, 185.1, 424/190.1, 193.1, 194.1, 197.11, 258.1, 278.1

[56] References Cited

U.S. PATENT DOCUMENTS 4,459,286  7/1984  Hilleman et al. .................. 424/258.1

FOREIGN PATENT DOCUMENTS

| 0 419 569 B1 | 4/1991 | European Pat. Off. |
| WO 92/08488 | 5/1992 | WIPO |
| WO 93/17712 | 9/1993 | WIPO |

OTHER PUBLICATIONS

Dick et al., "Glycoconjugates of Bacterial Carbohydrate Antigens," *Conjugate Vaccines* (Ed Cruse et al., S. Karger AG (Basel)) Contrib Microbiol Immunol 10:48114 (1989).
Van De Wisgert et al., "Immunogenicity of Stroptococcus...," Infection and Immunity 59:2750–2757 (1991).
Avery, O.T. and Goebel, W.F., "Chemo-immunological Studies on Conjugated Carbohydrate–Proteins," J. Exp. Med. 50:533–550 (1929).
Barrios, C. et al., "Mycobacterial Heat-shock Proteins as Carrier Molecules. II: The Use of the 70–kDa Mycobacterial Heat-shock Protein as Carrier for Conjugated Vaccines Can Circumvent the Need for Adjuvants and Bacillus Calmette Guérin Priming," Eur. J. Immunol. 22:1365–1372 (1992).
Brett, S.J. et al., "Differential Pattern of T Cell Recognition of the 65-kDa Mycobacterial Antigen Following Immunization with the Whole Protein or Peptides," Eur. J. Immunol. 19:1303–1310 (1989).

Cohen, I.R. and Young, D.B., "Autoimmunity, Microbial Immunity and the Immunological Homunculus," Immunology Today 12:105–110 (1991).
Cox et al., "Orientation of Epitopes Influences the Immunogenicity of Synthetic Peptide Dimers," Eur. J. Immunol. 18:2015–2019 (1988).
Elias, D. et al., "Induction and Therapy of Autoimmune Diabetes in the Non-obese Diabetic (NOD/Lt) Mouse by a 65-kDa Heat Shock Protein," Proc. Natl. Acad. Sci. USA 87:1576–1580 (1990).
Lamb, J.R. et al., "Mapping of T Cell Epitopes Using Recombinant Antigens and Synthetic Peptides," EMBO Journal 6:1245–1249 (1987).
Lussow, A.R. et al., "Towards Vaccine Optimisation," Immunol. Letters 25:255–264 (1990).
Lussow, A.R. et al., "Mycobacterial Heat-shock Proteins as Carrier Molecules,"Eur. J. Immunol. 21:2297–2302 (1991).
Merrifield, R.B., "Solid Phase Peptide Synthesis. I. The Synthesis of a Tetrapeptide," J. Am. Chem. Soc. 85:2149–2154 (1963).
Munk, M.E. et al., "T Cell Responses of Normal Individuals Towards Recombinant Protein Antigens of *Mycobacterium tuberculosis*," Eur. J. Immunol. 18:1835–1838 (1988).
Munk, M.E. et al., "T Lymphocytes from Healthy Individuals with Specificity to Self-epitopes Shares by the Mycobacterial and Human 65-Kilodalton Heat Shock Protein," J. Immunol. 143:2844–2849 (1989).
Pearson, C.M., "Experimental Models in Rheumatoid Disease," Arthritis and Rheumatism 7:80–86 (1964).
Szu, S.C. et al., "Comparative Immunogenicities of Vi Polysaccharide–Protein Conjugates Composed of Cholera Toxin or Its B Subunit as a Carrier Bound to High-or Lower–Molecular–Weight Vi," Infection and Immunity 57:3823–3827 (1989).
Verbon, A. et al., "Murine and Human B Cell Epitope Mapping of the *Mycobacterium tuberculosis* 10–kD Heat Shock Protein Using Overlapping Peptides," Clin. Exp. Immun. 86:6–11 (1991).
Young, D. et al., "Stress Proteins are Immune Targets in Leprosy and Tuberculosis," Proc. Natl. Acad. Sci. USA 85:4267–4270 (1988).

(List continued on next page.)

*Primary Examiner*—Michael P. Woodward
*Attorney, Agent, or Firm*—Pennie & Edmonds

[57] ABSTRACT

The invention relates to conjugates of poorly immunogenic antigens, e.g. peptides, proteins and polysaccharides, with a synthetic peptide carrier constituting a T cell epitope derived from the sequence of human heat shock protein hsp65, or an analog thereof, said peptide or analog being capable of increasing substantially the immunogenicity of the poorly immunogenic antigen. Suitable peptides according to the invention are Pep278h, which corresponds to positions 458–474 of human hsp65, and Pep II, which corresponds to positions 437–448 of human hsp65, but in which two cysteine residues at positions 442 and 447 are replaced serine residues.

25 Claims, 19 Drawing Sheets

OTHER PUBLICATIONS

Barrios, C., et al., 1992, Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming, *Chemical Abstracts* 117:632.

Bianco, A.E., et al. ,1986, A repetitive antigen of *Plasmodium falciparum* that is homologous to heat shock protein 70 of *Drosophila melanogaster*, *Proc. Natl. Acad. Sci. USA* 83:8713–8717.

Dostal, V.V., et al., 1977, Die Herpes–simplex–Virus–(HSV–1)–und HSV–2)Infektion, ihre klinische und onkogene Bedeutung, *Wiener klinische Wochenschrift* 89(22):741–748.

Edgington, S.M., 1995, Therapeutic Applications of Heat Shock Proteins, *Bio/technology* 13:1442–1444.

Hansen, K., et al., 1988, Immunochemical Characterization of and Isolation of the Gene for a *Borrelia burgdorferi* Immunodominant 60–Kilodalton Antigen Common to a Wide Range of Bacteria, *Infection and Immunity* 56(8):2047–2053.

Hedstrom, R., et al., 1987, A Major Immunogen In *Schistosoma mansoni* Infections Is Homologous To The Heat–Shock Protein Hsp70, *Jounal of Experimental Medicine* 165:1430–1435.

Hindersson, P., et al., 1987, Cloning and Expression of *Treponema pallidum* Common Antigen (Tp–4) in *Escherichia coli* K12, *Journal of General Microbiology* 133:587–596.

Husson, R.N., et al., 1987, Genes for the major protein antigens of *Mycobacterium tuberculosis*: The etiologic agents of tuberculosis and leprosy share an immunodominant antigen, *Proc. Natl. Acad. Sci. USA* 84:1679–1683.

Lamb, J.R., et al., 1989, Stress proteins may provide a link between the immune response to infection and autoimmunity,*International Immunology* 1(2):190–196.

Shinnick, T.M., et al., 1988, The *Mycobacterium tuberculosis* 65–Kilodalton Antigen Is a Heat Shock Protein Which Corresponds to Common Antigen and to the *Escherichia coli* GroEL Protein, *Infection and Immunity* 56(2):446–461.

Thole, J.E.R., et al., 1987, Characterization, Sequence Determination, and Immunogenicity of a 64–Kilodalton Protein of *Mycobacterium bovis* BCG Expressed in *Escherichia coli* K–12, *Infection and Immunity* 55(6):1466–1475.

Thole, J.E.R., et al., 1988, Antigenic relatedness of a strongly immunogenic 65 kDA mycobacterial protein antigen with a similarly sized ubiquitous bacterial common antigen, *Microbial Pathogenesis* 4:71–83.

Verloes, R., et al., 1981, Successful Immunotherapy With Micrococcus, BCG Or Related Polysaccharides On L1210 Leukaemia After BCNU Chemotherapy, *Br. J. Cancer* 43:201–209.

Vodkin, M.H., et al., 1988, A Heat Shock Operon in *Coxiella burnetii* Produces a Major Antigen Homologous to a Protein in Both Mycobacteria and *Escherichia coli*, *Journal of Bacteriology* 170(3):1227–1234.

Whittle, H.C., et al., 1987, Trials of intradermal hepatitis B vaccines in Gambian children, *Annals of Tropical Paediatrics* 7:6–9.

Yashphe, D.J., et al., 1969, Modulation of the immune response by a methanol extraction residue of BCG, *Isr. J. Med. Sci.* 5(3):440.

Young, D.B., 1988, Stress–Related Proteins Are Major Antigens In Leprosy And Tuberculosis, *UCLA Keystone Symposium* Abstract No. P432, p. 297.

Young, D., et al., 1989, Stress–Induced Proteins As Antigens In Infectious Diseases, *Stress–Induced Proteins*, pp. 275–285.

Zerial, A., et al., 1981, Effect of Immunostimulating Agents on Viral Infections, *Acta microbiol. Acad. Sci. hung.* 28:325–337.

Zykov, M.P., et al., 1981, Influenza Vaccine Response Following its Simultaneous Application with BCG, *Crkrank. Atm.–Org.* 156:203–211.

Zykov, M.P., et al., 1985, Modulation Of Humoral Immune Response To Influenze Vaccines By BCG, *Acta. virol.* 29:403–409.

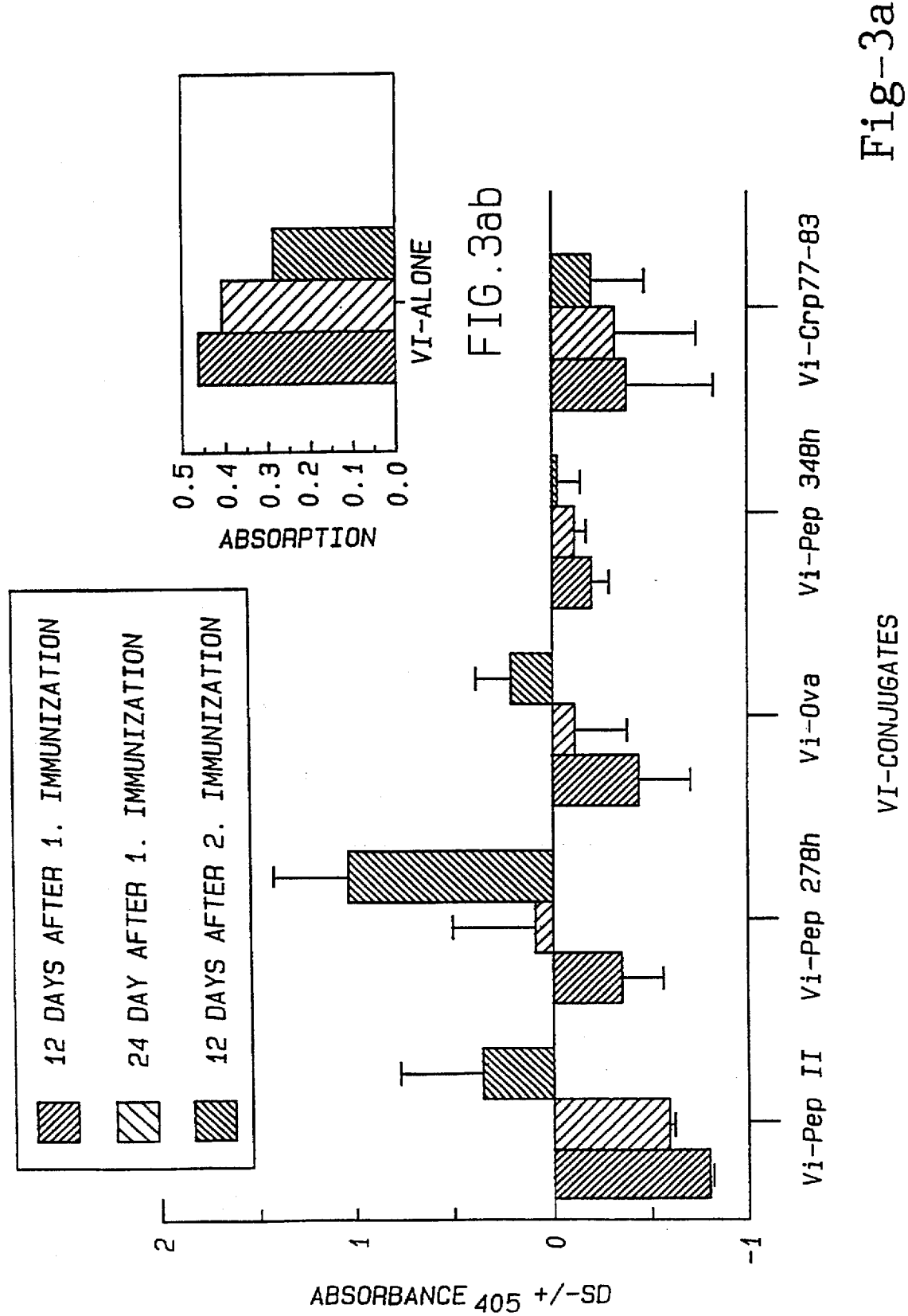

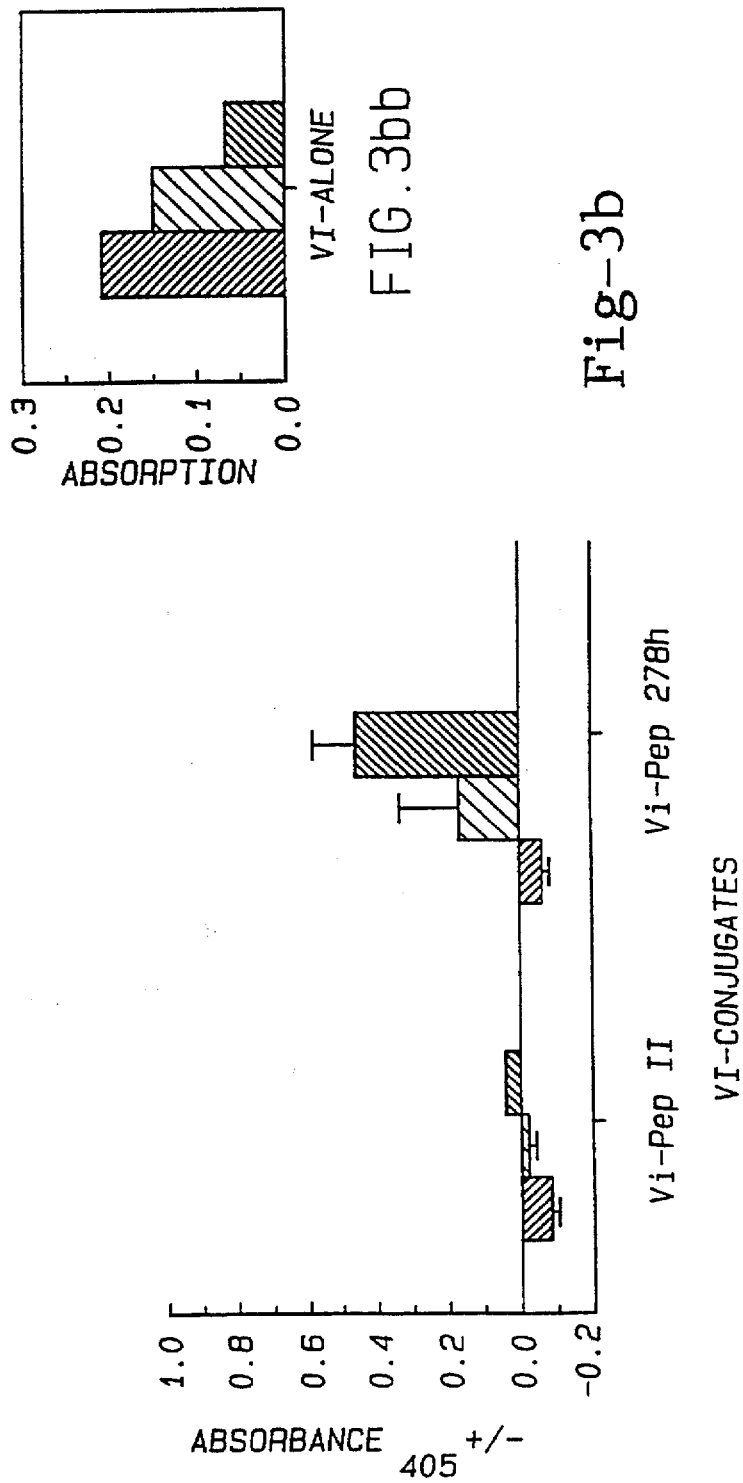

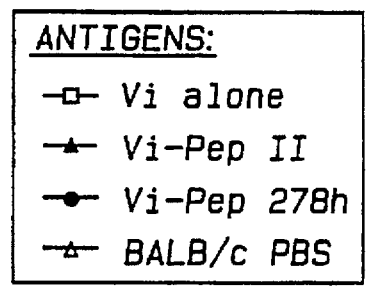
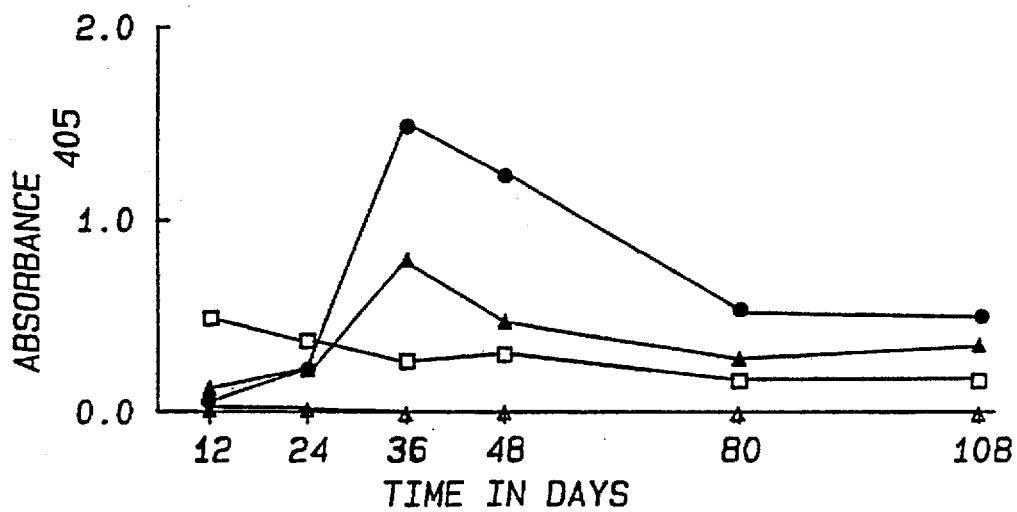
Fig-6a
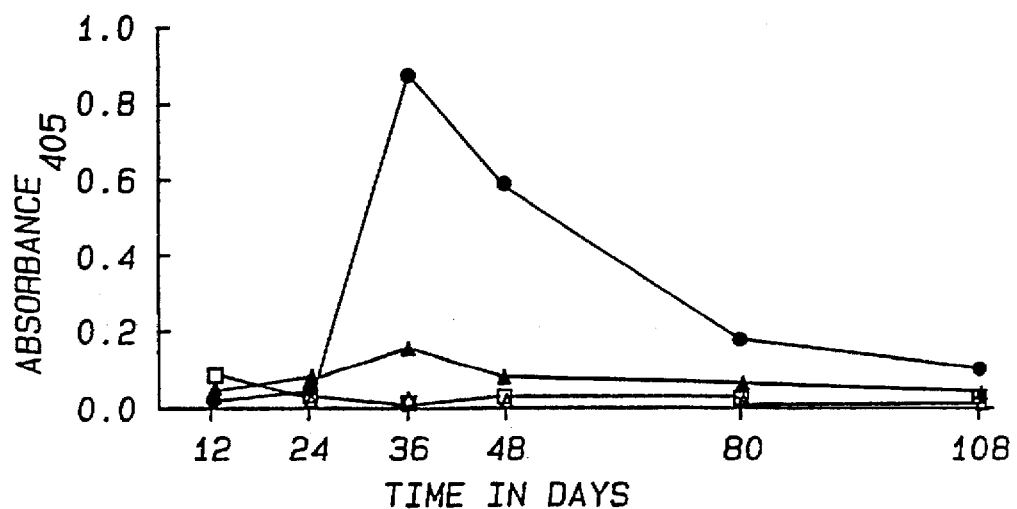
Fig-6b

CONJUGATES OF POORLY IMMUNOGENIC ANTIGENS AND SYNTHETIC PEPTIDE CARRIERS AND VACCINES COMPRISING THEM

FIELD OF THE INVENTION

The present invention relates to conjugates of enhanced immunogenicity based on synthetic peptide carriers constituting T cell epitopes, to their preparation and to vaccines suitable for immunization comprising said conjugates.

BACKGROUND OF THE INVENTION

Antibody responses have been subclassified into two main types on the basis of their requirement for T cells. The primary humoral immune response to T cell-dependent (T-dep) antigens is characterized by B and T cell activation and proliferation leading on one hand to the differentiation of plasma cells and immunoglobulin secretion, and on the other hand to the formation of germinal centers and immunological memory. Upon restimulation by antigen, these memory cells play the leading part in the secondary antibody response. The cardinal characteristics of the secondary response to T-dep antigens are rapidity of antibody production, greater magnitude of response as compared to the primary response, and an immunoglobulin class switch from IgM to IgG.

There are, however, a small number of antigens capable of activating B cells independently from T cell help referred to as T cell-independent (T-ind) antigens. They include among others bacterial capsular polysaccharides, like the capsular polysaccharide of *Streptococcus pneumoniae*, polymerized *Salmonella flagellin*, poly-D-amino acids and the *E. coli* lipopolysaccharide. T-ind antigens are characteristically of high molecular weight, with a repeating structure, and in most instances, are slowly degraded. They persist for long periods on the surface of specialized macrophages and can bind to antigen-specific B cells with great avidity through their multivalent attachment to the complementary immunoglobulin receptors which they crosslink. At high enough concentration, they have the ability to polyclonally activate a substantial proportion of the B cell pool, i.e. without reference to the antigen specificity of the surface receptor hypervariable region. In general, the T-ind antigens give rise to predominantly IgM responses, some IgG3 in the mouse, and relatively poor, if any, memory.

Capsulated bacteria such as *Haemophillus influenza* type b, *Streptococcus pneumoniae*, *Neisseria meningitidis*, group B Streptococci, and *E. coli* type K1, cause serious invasive diseases in humans, especially in infants and in immunocompromised individuals. Plasma anti-polysaccharide antibodies have been shown to be protective against invasive diseases caused by most of these pathogens and vaccines consisting of purified capsular polysaccharides (CPS) have been developed to induce such antibodies in the individuals at risk. Polysaccharides are, however, poor immunogens in infants, and their use as vaccines is seriously hampered by this fact. The reason for their poor immunogenicity is believed to be related to their belonging to the group of T-ind antigens.

The discovery by Avery & Goebel (1929) that coupling of polysaccharides to protein carriers increases immunogenicity has recently been used for the preparation of vaccines for human use. Both in humans and in rodents these conjugates behave like T-dep antigens by exhibiting induction of immunological memory. There are similarities between conjugate polysaccharide vaccines and protein carrier-hapten systems.

Thus the CPS conjugates are able to induce protective levels of CPS antibodies in infants, while CPS alone is not. It is possible that the superior immunogenicity of conjugates compared to that of pure polysaccharides is due to the help by carrier-specific T cells, as has been demonstrated in the carrier-hapten system in rodents.

In most cases, T-ind antigens have been coupled to large immunogenic proteins such as tetanus toxoid, cholera toxin or diptheria toxoid. Nevertheless, the immunological response to high molecular weight carrier molecules harboring stimulatory as well as suppressive T cell epitopes are not very predictable. It has been shown that the antibody response to a hapten coupled to a carrier protein can also be inhibited when the recipient has been previously immunized with the unmodified protein. This phenomenon has been termed carrier-induced epitope suppression and was recently demonstrated to occur with a number of hapten-protein conjugates. Since the development of more potent conjugate vaccines against a large number of extremely infectious organisms is still important, efforts are being made to search for more appropriate carrier molecules providing the needed T cell epitopes. Universally immunogenic T cell epitopes, defined by specific peptides with sharply outlined immunological characteristics, might represent a new generation of such alternative molecules. Proteins well recognized by the immune system might be an appropriate source for peptides serving this purpose.

Studies using a wide variety of proteins, both those closely related to self and those phylogenetically distantly related, have shown that the majority of T cells are focused onto a few immunodominant epitopes with a minority responding to other, subdominant determinants. This hierarchy of determinant utilization by T cells could result from a combination of factors including differential affinities for the available MHC molecules, the diversity of the T cell repertoire, internal competition for MHC-binding sites and fine differences in processing.

Evidence is accumulating that proteins belonging to the family of heat shock proteins (hsp's) are major antigens of many pathogens (Young et al, 1988). Hsp's were first described and later named due to their production by cells exposed to sudden elevations in temperature. The hsp's include proteins of various molecular weights, including 20 kD, 60 kD, 65–68 kD, 70 kD, 90 kD, 110 kD, and others. It is now apparent that hsp's are induced in all cells by many different environmental insults, including oxidative injury, nutrient depletion and infection with intercellular pathogens; the hsp response enables the cell to survive under otherwise unfavorable conditions. Although cellular stress increases the synthesis of hsp's, many hsp's are also constitutively expressed and play an essential role in normal cell function. The hsp response is ubiquitous throughout the pro- and eukaryotic kingdoms and hsp's belong to some of the most conserved molecules. Despite evolutionary divergence of over a billion years, the human and the mycobacterial hsp65 molecules, for example, are identical in about 50% of their amino acid residues. This chemical conservation includes many stretches of amino acid of full or near identity. Consequently, every organism will necessarily share immunological cross-reactivity with the hsp65 of any foreign cell. Hence, the hsp65 molecule of any infectious cellular agent will be part self and part non-self to any host with an immune system. For these reasons, hsp65 and other hsp's would be predicted to be poorly immunogenic. Quite to the contrary, evidence suggests that hsp's may be some of the most dominant immunogens.

Hsp65, as a representative member of the proteins belonging to the hsp family, can be considered to be a dominant antigen because infection or immunization with many ..different bacteria induces antibodies and T cells specific for the hsp65 molecule (Young et al, 1988). In mice immunized with *Mycobacterium tuberculosis*, 20% of all T cells which respond to the bacterium, are specific for hsp65. Interestingly, T cells with reactivity to hsp65 have also been identified in normal healthy individuals lacking any clinical signs of disease (Munk et al, 1988). Using synthetic peptides, Lamb et al. (1987) and Munk et al. (1988) showed T cell responses to shared epitopes of the mycobacterial and human hsp65; this formally proved the existence of T cells to self epitopes of hsp65 in normal individuals.

As a consequence of this immunodominance, it is not surprising that the hsp65 molecule seems to be involved in autoimmunological events. Immunity to hsp65 can cause autoimmune diabetes in mice and may be related to autoimmune arthritis in rats and in humans (Elias et al, 1990; Pearson, 1964). Therefore, immunity to hsp65 is associated with autoimmune disease, but it is also associated with a state of health.

During an infection, both pathogen and host increase dramatically their synthesis of hsp's to protect against stresses imposed by the other. In analog with B cell responses to autoantigens, it is possible to envisage that self hsp-reactive T cells, like T cells specifically recognizing hsp65, could be engaged beneficially in the resolution of inflammation by removal of stressed cells. Perhaps, however, autoimmune disease could occur if this response is not correctly regulated. Cohen & Young (1991) suggested the prevalence of "natural immunity" in healthy individuals ensured by an immune system based on a series of highly controlled and regulated immune networks directed against a limited number of controlled self antigens. The hsp65 molecule is suggested to be one of these antigens to which such a highly organized immune response exists naturally (Elias et al, 1990).

Cox et al. (1988) showed that a dimer of the 65–85 peptide of *Mycobacterium tuberculosis* 65 kDa protein did not affect its ability to induce T cell proliferation, but it enhanced antibody production, and suggested that combination of heterologous peptides with the N-terminal of the mycobacterial 65–85 sequence may be generally applicable for the potentiation of peptide vaccines. Lussow et al. (1990) and Barrios et al. (1992) showed that the hsp65 and the hsp70 of *Mycobacterium boris* can act as carrier molecules for the induction of anti-hapten antibodies in mice. In addition, many T cell epitopes on *M. bovis* hsp65 have been identified, and the entire protein has been demonstrated to be immunogenic in a wide variety of mouse strains with differing MHC haplo-types (Brett et al, 1989).

It can be assumed that some T cell epitopes within the sequence of the hsp65 protein (of host and parasite, respectively) show immunodominance and are able to induce immunological memory, whereas others do not express privileged immunological recognition or are involved in the induction of autoimmunity. Distinguishing between these functional different T cell epitopes may lead to the identification of universally immunogenic peptides, which can quality as safe, defined, and potent alternatives for carrier molecules of T-ind antigens.

European Patent EP 262 710 and U.S. Pat. No. 5,154,923 describe peptides having an amino acid sequence corresponding to positions 171–240 and 172–192, respectively, of a *Mycobacterium boris* BCG 64 kD polypeptide, that are useful as immunogens inducing resistance to autoimmune arthritis and similar autoimmune diseases.

PCT Patent Application No. WO 90/10449 describes a peptide designated p277 having an amino acid sequence corresponding to positions 437–460 of the human hsp65 molecule that is useful as immunogen inducing resistance to insulin dependent diabetes mellitus (IDDM). A control peptide, designated p278, corresponding to positions 458–474 of human hsp65, did not induce resistance to IDDM.

Lussow et al. (1990) showed that the priming of mice with live *Mycobacterium tuberculosis* var. bovis (BCG) and immunization with the repetitive malaria synthetic peptide $(NANP)_{40}$ conjugated to purified protein derivative (PPD), led to the induction of high and long-lasting titers of anti-peptide IgG antibodies. Later on, Lussow et al. (1991) showed that mycobacterial heat-shock proteins (hsp) of 65 kDa (GroEL-type) and 70 kDa (DnaK-type) acted as carrier molecules in mice, previously primed with *Mycobacterium tuberculosis* var. boris (bacillus Calmette-Guerin, BCG), for the induction of high and long-lasting titers of IgG against the repetitive malaria synthetic peptide $(NANP)_{40}$. Anti-peptide antibodies were induced when the malaria peptide, conjugated to the mycobacterial hsp, was given in the absence of any adjuvants.

Barrios et al. (1992) have shown that mice immunized with peptides or oligosaccharides conjugated to the 70 kDa hsp produced high titers of IgG antibodies in the absence of any previous priming with BCG. The anti-peptide antibody response persisted for at least 1 year. This adjuvant-free carrier effect of the 70 kDa hsp was T cell dependent, since no anti-peptide nor anti-70 kDa IgG antibodies were induced in athymic nu/nu mice. Previous immunization of mice with the 65 kDa or 70 kDa hsp did not have any negative effect on the induction of anti-peptide IgG antibodies after immunization with hsp-peptide conjugates in the absence of adjuvants. Furthermore, preimmunization with the 65 kDa hsp could substitute for BCG in providing an effective priming for the induction of anti-$(NANP)_{40}$ antibodies. Finally, both the 65 kDa and 70 kDa hsp acted as carrier molecules for the induction of IgG antibodies to group C meningococcal oligosaccharides, in the absence of adjuvants, suggesting that the use of hsp's as carriers in conjugated constructs for the induction of anti-peptide and anti-oligosaccharide antibodies could be of value in the design of new vaccines for eventual use in humans.

None of the above mentioned references describe specific T cell epitopes of human hsp65 conjugated to poorly immunogenic molecules.

SUMMARY OF TEE INVENTION

It is an object of the present invention to provide a method for enhancing the immunogenicity of poorly immunogenic antigen molecules, thus converting them to suitable antigens for immunization.

For this purpose, the present invention provides conjugates of a poorly immunogenic antigen and a synthetic peptide carrier constituting a T cell epitope derived from the sequence of human hsp65, or an analog thereof, said peptide or analog being capable of increasing substantially the immunogenicity of the poorly immunogenic antigen.

Mammalian, including human and mouse hsp65, are often designated "hsp60" by other authors, because they belong to the hsp60 generic family. In this specification, whenever human or mouse hsp65 is mentioned, it is intended to encompass these molecules with the designation "hsp60" or any other designation given to them in the art.

Any peptide, or analog thereof, derived from human hsp65 constituting a T cell epitope and able to increase substantially the immunogenicity of the poorly immunogenic antigen, can be used in the invention.

A preferred peptide according to the invention, herein designated Pep278h or 278h, corresponds to positions 458–474 of the human hsp65 molecule, and has the sequence:

```
458                             474
N E D Q K I G I E I I K R T L K I
```

Preferred analogs of Pep278h are the peptides herein designated Pep278m or 278m, in which the residue $T^{471}$ of Pep278h is replaced by $A^{471}$, and Pep278mt or 278mt, of the following sequence:

```
E G D E A T G A N I V K V A L E A
```

Another T cell epitope according to the invention derived from the human hsp65 molecule, herein designated Peptide II or Pep II, corresponds to positions 437–448 of the human hsp65 molecule in which the two cysteine moieties at positions 442 and 447 have been replaced by serine, and has the sequence:

```
437              448
V L G G G S A L L R S I
```

The poorly immunogenic antigen molecule may be a peptide, a polypeptide or a protein, e.g., a peptide derived from HIV virus or from malaria antigen, or a bacterial polysaccharide, e.g., capsular polysaccharides from *Haemophilus influenzae* type b, *Streptococcus pneumoniae*, *Neisseria meningitidis*, group B Streptococci, *E. coli* type K1, Salmonella, such as *Salmonella typhi*, etc.

The carrier peptide is covalently linked to the poorly immunogenic antigen molecule, either directly or through a spacer.

The invention further relates to vaccines comprising a conjugate of the invention or a mixture of the poorly immunogenic antigen and the suitable peptide carrier.

In another embodiment the invention relates to a method of immunization of a mammalian host which comprises administering to said host an effective amount of a conjugate of the invention, or co-administering effective amounts of a poorly immunogenic antigen molecule and of a synthetic peptide carrier constituting a T cell epitope derived from the sequence of human hsp65, or an analog thereof, said peptide or analog being able to enhance substantially the immunogenicity of the poorly immunogenic antigen.

BRIEF DESCRIPTION OF THE DRAWINGS

FIGS. 3a, 3ab, 3b, 3bb show kinetics of anti-Vi antibody production induced by Vi-protein/peptide conjugates (3a and 3b) and Vi alone (3ab and 3bb) (2.5 µg (FIGS. 3a and 3ab) and 0.25 µg (FIGS. 3b and 3bb) Vi injected per mouse, 12 and 24 days after first immunization and 12 days after second immunization.

FIG. 5a–anti-Vi IgM isotype response to Vi and Vi-Pep278h; FIG. 5b–anti-Vi IgG isotype response to Vi and Vi-Pep278h.

FIGS. 6A–B illustrate time course of anti-Vi antibody production in mice immunized with Vi alone or with conjugates Vi-Pep II and Vi-Pep278h, at serum dilution 1:100 (FIG. 6a) and 1:1000 (FIG. 6b).

FIG. 12a: response of BALB/c mice to Vi, Vi-278h, Vi-278m, Vi-278mt, Vi-SRes, Vi-348 and Vi-277(S); FIG. 12b: response of BALB/k mice to Vi, Vi-278h, Vi-278m, Vi-278mt Vi-277(S) and Vi-SRes; 12c: response of BALB/b mice to same antigens of FIG. 12b; FIG. 12d: response of NOD mice to Vi, Vi-278h, Vi-278m, Vi-278mt and Vi-SRes; FIG. 12e: response of NON.NOD mice to Vi, Vi-278h and Vi-278mt.

DETAILED DESCRIPTION OF THE INVENTION

Figure 1:
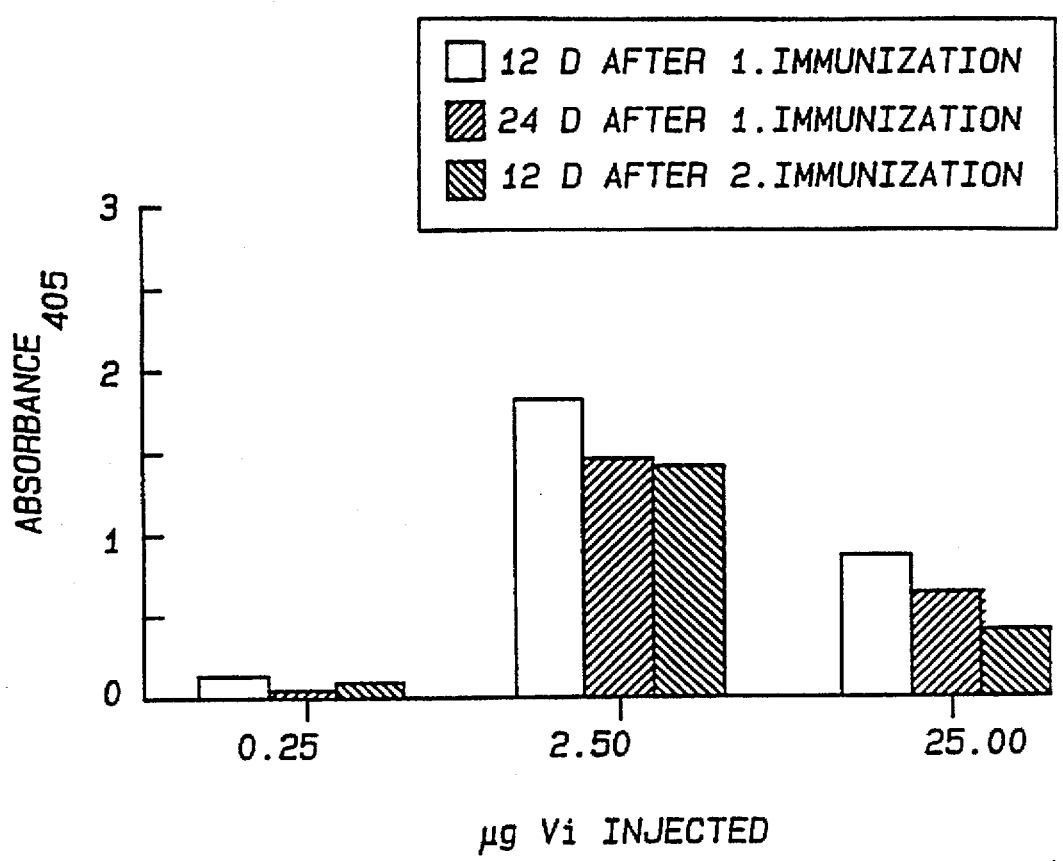
FIGS. 1–1a show serum anti-Vi antibody response induced in mice by Vi alone, 12 and 24 days after first immunization and 12 days after second immunization, at serum dilution of 1:50 (1) and 1:500 (1a).

Preferred conjugates according to the invention are formed by covalently linking Pep278h or Pep II with a bacterial polysaccharide, e.g., the CPS Vi of *Salmonella typhi*, hereinafter referred to as Vi, a linear homopolymer of poly-α-(1–4)GalNAc variably O-acetylated at the $C_3$-position, as shown in Scheme 1. Vi alone, like other CPSs, does not elicit a booster response in mammals, both animals and humans, when reinjected, but its immunogenicity is increased when presented as a conjugate according to the invention coupled to a suitable peptide derived from human hsp65 or an analog thereof, or in mixture with such a peptide or analog. Reinjection of the Vi-peptide conjugate induces an increase in the level of anti-Vi antibodies (booster effect), which are mainly represented by the IgG isotype.

In the case of Pep278h, the active peptides according to the invention are characterized as being highly charged, i.e. of strong electric properties (7 out of 17 constituent amino acid residues of Pep278h are either negatively or positively charged) and highly hydrophobic (6 amino acid residues). The peptide Pep278h is further characterized as possessing a polar negatively-charged N-terminal domain, a polar positively-charged C-terminal domain and a highly hydrophobic core. These overall features should be maintained in order to preserve efficacy. Thus, following the above general outline certain amino acids substitution will lead to active peptides. More specifically, positions 6,8,10,11,15 and 17 in the Pep278h peptide chain (corresponding to positions 463, 465, 467, 468, 472 and 474 of the human hsp65 molecule) can be occupied by either I or L or by other hydrophobic amino acids, natural, such as V, M, or F, or unnatural amino acids, such as norleucine (Nle) or norvaline (Nva). Positions 5,12,13 and 16 in the Pep278h chain (corresponding to positions 462, 469, 470 and 473 of the human hsp65 molecule) can be occupied by either K or R or by unnatural positively charged amino acids, such as ornithine (Orn). Interchange of E and D may also lead to active derivatives.

The term "analogs" in the present invention relates to peptides obtained by replacement, deletion or addition of amino acid residues to the sequence of the T cell epitope, as long as they have the capability of enhancing substantially the immunogenicity of poorly immunogenic antigen molecules. For example, stable derivatives can be obtained by replacing original cysteine residues by serine residues, as in the case of Pep II. Analogs, in the case of Pep278h, are peptides such that at least 70%, preferably 90–100%, of the electric properties and of the hydrophobicity of the peptide molecule are conserved. These peptides can be obtained according to the instructions in the paragraph hereinbefore.

The peptides according to the invention may have all the optically active amino acid residues in L or in D form, or some of the amino acid residues are in L and others are in D form.

By "substantially increasing the immunogenicity of a poorly immunogenic antigen molecule" it is meant to comprise both the induction of an increase in the level of antibodies against said antigen as well as the presentation of said antibodies as mainly of the IgG isotype.

The peptide carrier may be linked to the antigen molecule directly or through a spacer.

A direct link between the peptide and Vi is shown in Scheme 1 herein, where the conjugate

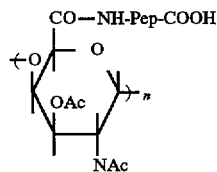

is obtained by Procedure 3 described hereafter.

The spacer may have the formula —O—R—CO— or —NH—R—CO—, thus forming an ester or amide, respectively, with the carboxy group of Vi and a peptide bond with the terminal amino group of the peptide; —O—R—NH— or —NH—R—NH—, thus forming an ester or amide, respectively, with the carboxyl group of Vi and an amide with the terminal carboxyl group of the peptide; of —NH—R—$CH_2$—, wherein R is a saturated or unsaturated hydrocarbon chain optionally substituted and/or interrupted by one or more aromatic radicals or by heteroatoms such as O, S or N. Preferably, R is an aliphatic hydrocarbon chain containing 3–16 carbon atoms, such as the residue of ε-aminocaproic acid.

The conjugate of the formula:

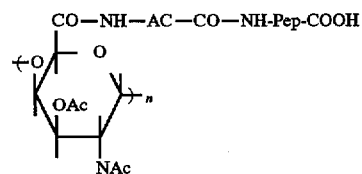

in which Ac is acetyl, AC is the residue of ε-aminocaproic acid, Pep is the residue of the peptide carrier Pep278h or Pep II and the saccharide residue represents a repeating unit of the Vi capsular polysaccharide of *Salmonella typhi*, may be prepared by three different procedures 1, 2 and 4 depicted in Scheme 1 and described in detail hereinafter.

The conjugates wherein the spacer is —NH—R—$CH_2$— are obtained by reduction of —NH—R—CO— groups.

The invention further relates to vaccines comprising a conjugate of the invention. These vaccines will preferably be administered via the subcutaneous route in suitable vehicles for human and veterinary purposes.

The invention will now be illustrated by the following non-limiting examples:

EXAMPLES

In the examples, the following materials and methods will be used.

MATERIALS & METHODS a. Materials: All solvents and chemicals were of analytical grade and obtained from Aldrich, U.S.A., unless otherwise mentioned.

b. Peptide synthesis: Peptides were obtained by solid phase synthesis using the t-Boc protection group for terminal amino groups. Merrifield resin with 0.5–0.7 meq/g. of active chlorine per g was purchased from Chemalog, N.J., U.S.A. Boc-protected amino acids with appropriate side chain protections were purchased from Baechem, Ca., U.S.A. Coupling of the first amino acids to resin was performed via cesium salts of amino acid derivatives. Peptide chain extension was carried out manually according to the general principles of the solid phase methodology (Merrifield, 1963). Cleavage of peptides from the resin and side chain deprotection was done by the HF procedure. The sequences of the peptides and analogs synthesized are in Table 1.

The analog peptide 278m corresponds to positions 458–474 of mouse hsp65 and the analog 278mt corresponds to positions 431–447 of mycobacterial hsp65.

The following control peptides were also synthesized: peptide 277(S), an analog of peptide p277 corresponding to positions 437–460 of human hsp65 (WO 90/10449), in which the Cys (C) residues at positions 342 and 347 were replaced by Ser (S) residues; peptide 348h corresponding to positions 449–460 of human hsp65; peptide CRP 77–83 corresponding to positions 77–83 of human C-reactive protein, and peptide SerRes, derived from sea urchin.

Peptides II, 277(S), SerRes, 278mt and CRP 77–83 were synthesized as above. Peptides 278h, 278m and 348h were produced with an automated synthesizer (Applied Biosystem model 430A) using the company's protocols for t-butytoxycarbonyl (t-Boc) strategy.

c. Reversed-phase HPLC: Final purification of peptide products was performed using the semi-preparative HPLC column RP18 (Merck, Darmstadt, Germany) employing the SP8750 liquid chromatography system equipped with a SP8733 variable wavelength detector in water-acetonitrile gradients containing 0.1% trifluoroacetic acid (TFA). The effluents were monitored by UV absorbance at 220 nm. Acetonitrile of HPLC grade was purchased from Merck (Darmstadt, Germany). HPLC-pure peptides were characterized by amino acid analysis.

d. Vi : The Vi purified from *Citrobacter freundii* WR7011 (kindly donated by J. B. Robbins and S. C. Szu, National Institute of Health, Bethesda, Md.) contained <1% (each) protein, nucleic acid, and lipopolysaccharide. The molecular size of the Vi was estimated to be $3 \times 10^3$ kDa.

TABLE 1

Sequences of synthetic peptides

| No. | Peptide Origin | Peptide Name | Sequence |
|---|---|---|---|
| 1 | Human hsp65 (458–474) | 278h | NEDQKIGIEIIKRTLKI (SEQ ID NO:1) |
| 2 | hsp65 analog | 278m | NEDQKIGIEIIKRALKI (SEQ ID NO:2) |
| 3 | hsp65 analog | 278mt | EGDEATGANIVKVALEA (SEQ ID NO:3) |
| 4 | Human hsp65 (437–448) | pepII | VLGGGSALLRSI (SEQ ID NO:4) |
| 5* | | 277(S)** | VLGGGSALLRSIPALDSLTPANED (SEQ ID NO:5) |
| 6 | Human hsp65 (449–460) | 348h | PALDSLTPANED (SEQ ID NO:6) |
| 7 | Human C-Reactive Protein (77–83) | CRP77–83 | VGGSEIL (SEQ ID NO:7) |
| 8 | Sea Urchin | SerRes | LRGGGVCGPAGPAGTVCS (SEQ ID NO:8) |

*Peptides No. 5, 6, 7 and 8 were used as controls
**Peptide 277 (S) is a stable analog of peptide 277 (WO 90/10449) corresponding to position 437–460 of human hsp65 in which cysteine residues (C) at positions 442 and 447 have been replaced by serine (S) residues.

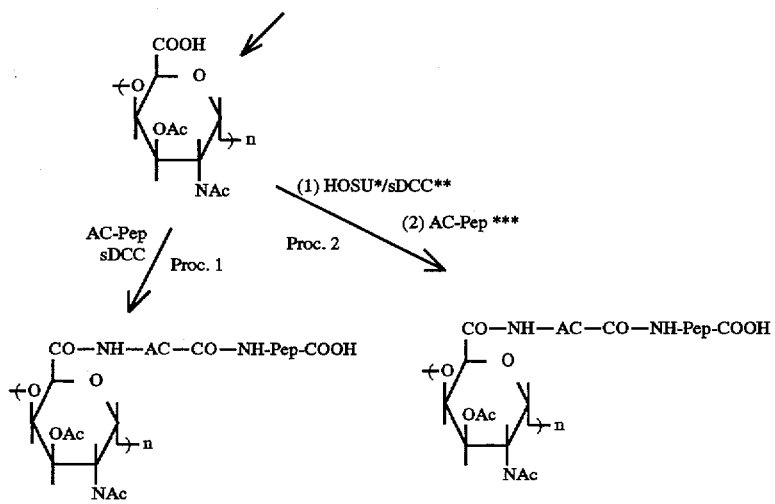

Scheme 1: coupling procedures

-continued
Scheme 1: coupling procedures

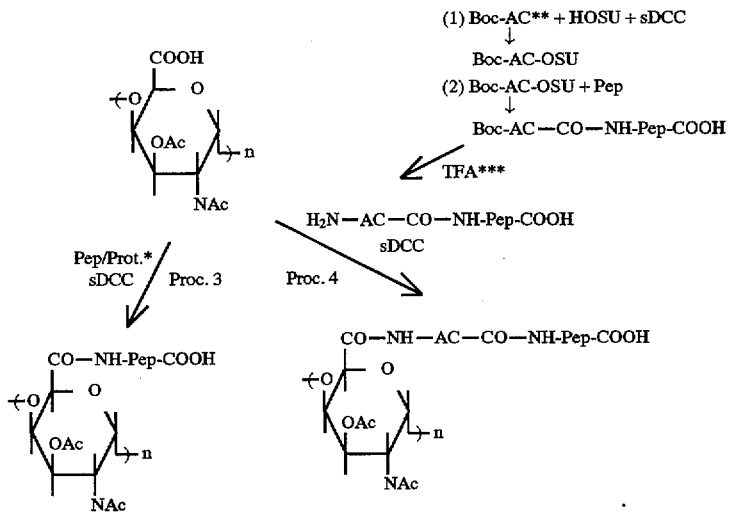

* Pep/Prot. = Peptide/Protein
** Boc-AC = Boc-ε-Amino Caproic Acid
*** TFA = Trifluoracetic Acid e. Conjugation of Vi and synthetic peptides: The different conjugation procedures are summarized in Scheme 1.

Procedure 1:

Coupling of Vi and peptide via spacer (a): During solid phase synthesis, Peptide II was extended at the N-terminus, using usual procedure for addition of an amino acid residue, by t-Boc-ε-amino caproic acid (AC), acting as spacer in the Vi-peptide conjugate. Equal amounts of Vi and Peptide II-AC were dissolved in a minimal volume of double distilled water (ddw) and the pH adjusted to about 6. Two equivalents (eqv.) of water-soluble carbodiimide (CDI;1-(3-dimethylaminopropyl)-3-ethylcarbodiimide hydrochloride) were added twice in an interval of several hours and the reaction mixture left for incubation over night (ON). The crude conjugate was dialysed against phosphate buffered saline (PBS) and the peptide density in Vi, i.e., the extent of peptide bound to Vi, was determined by amino acid analysis (see Table 2).

Evaluation of the amount of Vi covalently bound to the peptide was carried out by Fourier-transformed infrared (FTIR) spectroscopy.

Procedure 2:

Coupling of N-hydroxysuccinimide-activated Vi and peptide via spacer. Before conjugating to Peptide II-AC, the carboxylic-functions of Vi were activated by a, reaction with N-hydroxysuccinimide (Sigma). One eqv. Vi was suspended in NMP (N-Methyl-Pyrrolidone, Riedel De. Haen, Germany), vortexed and centrifuged for 5 min in an Eppendorf centrifuge. The pellet was resuspended in NMP, followed by addition of 5 eqv. each of N-hydroxysuccinimide and water-soluble carbidiimide(CDI), respectively, and incubated under gentle stirring. After few hours, the reaction mixture was centrifuged and the supernatant containing the N-hydroxysuccinimide ester of Vi, was mixed with 1 eqv. Peptide II-Ac dissolved in aqueous solution at a pH of 7.5. After a few hours of incubation the conjugate was dialysed against ddw and the peptide density was determined by amino acid analysis (see Table 2).

TABLE 2

Conjugates used as immunogens

| Vi-peptide conjugate | Coupling procedure[1] | Peptide/Vi monomer[2] (molar ratio) |
|---|---|---|
| Vi-Pep II | 1 | 1/127 |
| Vi-Pep II* | 2 | 1/400 |
| Vi-Pep 278h | 3 | 1/25 |
| Vi-Pep 348h | 3 | 1/22 |
| Vi-Pep CRP77-83 | 4 | 1/14 |
| Vi-Pep 277(S) | 4 | 1/10 |
| Vi-Ova[3] | 3 | 1/175 |

[1] Coupling procedure 1–4 described in Material & Methods
[2] The peptide density was determined by amino acid analysis
[3] Ova = Ovalbumin

TABLE 3

Amount of conjugated peptide injected per mouse

| Vi-Peptide conjugate | Injected amount of peptide/mouse |
|---|---|
| a) in immunization with 0.25 μg conjugated Vi per mouse | |
| Vi-Pep II | 0.010 μg |
| Vi-Pep 278h | 0.170 μg |
| b) in immunization with 2.50 μg conjugated Vi per mouse | |
| Vi-Pep II | 0.100 μg |
| Vi-Pep II* | 0.030 μg |
| Vi-Pep 278h | 1.000 μg |
| Vi-Pep 348h | 0.600 μg |
| Vi-Pep CRP 77-83 | 0.510 μg |
| Vi-Pep 277(S) | 2.200 μg |
| Vi + Pep II (mixed) | 2.500 μg |
| Vi-Ova | 2.200 μg |

Procedure 3:

Conjugation of Vi and protein/peptide without a spacer. One eqv. Vi and 1 eqv. protein/peptide were dissolved in a minimal volume of ddw and incubated for 12 hours at room temperature (RT) at pH 6 in the presence of 2 eqv. water-soluble CDI (for conjugating peptides) and 60 eqv. water-soluble CDI (in the case of protein), respectively. After dialysis of the reaction mixture, the protein/peptide density in the conjugate was determined by amino acid analysis (see Table 2).

Procedure 4:

Coupling of Vi and peptide following extension of peptide chain by a spacer in solution (b). In order to activate the carboxyl function of t-Boc-ε-amino caproic acid ( t-Boc-AC) by N-hydroxysuccinimide, 1 mmol t-Boc-AC was mixed with 1.15 mmol N-hydroxysuccinimide in a minimal volume of dioxane (Merck, Germany); 1.15 mmol N,N'-dicyclohexylcarbodiimide (DCC) dissolved in dioxane was added, and after 3 hours the reaction mixture was filtered and washed with dioxane. 0.1 mmol of the desired peptide was dissolved in a small amount of ddw and mixed with 0.2 mmol $KHCO_3$ (Merck). The solution of the N-hydroxysuccinimide ester of t-Boc-AC and the prepared peptide solution were mixed and reacted for 1 hour with vigorous mixing. The reaction mixture was then diluted with ddw (10 ml), cooled and acidified with 1N $KHSO_4$ solution. The product was extracted by ethyl acetate. The organic solution was washed with ddw, dried over $Na_2SO_4$ and evaporated to dryness. After drying the product for 2 hours over $P_2O_5$, dissolving it with 4–5 ml TFA (Merck) and reacting for 10 min, the liquid was evaporated in vacuum ale 30° C. The compound was washed twice with $CH_2Cl_2$ and the fluid evaporated before drying 2–3 hours over $P_2O_5$. Subsequently, the peptide-AC product was dissolved in ddw and the pH adjusted to 8. Five mg N-hydroxysuccinimide ester of Vi (prepared as described in Procedure 2) were added. After several hours of incubation, the resulting Vi-AC-Peptide conjugate was dialysed against ddw. The peptide density in the conjugate was estimated by amino acid analysis and the results are presented in Table 2.

f. Conjugation of Vi fragments and synthetic peptides. The Vi fragments (kindly provided by Dominique Schulz, Pasteur-Merieux, France) were coupled to synthetic peptides as described in Procedure 3 above.

g. Conjugation of the all D synthetic polypeptide poly (Phe, DGlu)-poly(Pro)-poly(Lys) (hereafter referred to as FEPK) and synthetic hsp65 peptides. The synthetic random branched polypeptide FEPK (kindly provided by the group of Prof's Edna Mozes and Michael Sela, Weizmann Institute of Science, Israel) was coupled to the synthetic hsp65 peptides by Procedure 3.

h. Immunization. BALB/c female mice (obtained from Olac), 2–3 months old, were immunized subcutaneously (sc) and intramuscularly (im), respectively, one, two or three times at 12-day intervals with Vi alone, with Vi-conjugate, or with Vi mixed with peptide. The injected amount of antigen as well as the adjuvant used, varied from experiment to experiment. Mice from each experimental group were exsanguinated 12 days after each injection (72 days after the last injection for: long-term follow-up of anti-Vi antibody production).

i. Serology. Vi antibody levels elicited in mice with native or conjugated Vi, were determined by an enzyme-linked immunosorbent assay (ELISA). Since negatively charged polysaccharides do not attach well to the polystyrene commonly used in the solid-phase ELISA, positively charged methylated bovine serum albumin (BSA) was used to coat Vi on the solid surface with very little non-specific binding. In detail, 0.5 mg Vi were dissolved in 1 ml PBS and stirred for 1 hour at RT. Ten mg methylated BSA (Sigma) were suspended in 1 ml $H_2O$ and the obtained solution filtered on a 0.8 μm filter. To prepare the coating solution, 1 ml of dissolved polysaccharide was stirred for 20 min at RT with 50 μl of the methylated BSA solution and subsequently diluted 1:20 in PBS. Nunclon delta Si microwell plates were coated for 3 hours at 37° C. with 100 μl coating solution per well (2.5 μg Vi/well). The plates were washed 5 times with PBS containing 0.33% Brij35 (Sigma) and blocked with a solution of PBS and 1% dried skimmed milk for 2 hours at 37° C. After washing, 100 μl aliquots of diluted unknown sere and of diluted standard serum (dilution buffer containing 1% skimmed milk and 0.33% Brij35 in PBS) were added and the plates were incubated for 1 hour at 37° C. Reference and test sera were applied to the plates in duplicate. The non-bound antibodies were removed by washing and an appropriate dilution of goat anti-mouse IgG $Fab_2$-alkaline phosphatase conjugate (Sigma), in the case of test sera, and goat anti-horse IgG $Fab_2$ enzyme conjugate (Sigma), in the case of the standard serum, was added to the plates (100 μl per well). After an incubation of 2 hours at 37° C., the plates were washed and the color was developed with the addition of 100 μl substrate solution containing 0.6 mg/ml of p-nitrophenylphosphate (Sigma) in diethanolamine-$H_2O$ pH 9.8. The enzyme reaction was stopped 20 min later by the addition of 10 μl 5N NaOH per well. Optical densities were read at 405 nm. The anti-Vi standard serum Burro 260, containing 550 mg Vi antibody/ml, was prepared by multiple intravenous injections of formalin-fixed *S. typhi* Ty2 (kindly donated by J. B. Robbins and S. C. Szu, NIH, Maryland). The results obtained are expressed as optical density read at 405 nm or as μg Vi antibody/ml.

EXAMPLES

Example 1

Preparation of Vi-peptide/protein conjugates.

Conjugates of Vi with peptide II were prepared by coupling procedure 1 (Vi-Pep III) or 2 (Vi-Pep II*). Conjugates of Vi with peptides 278, 278m, 278mt, 348h and ovalbumin (Ova) were prepared by coupling procedure 3, and conjugates of Vi with CRP 77–83 and 277(S) by coupling procedure 4.

The composition of some of the Vi-conjugates was determined by amine acid analysis. The results presented in Table 2 indicate that the molar ratio of peptide/protein per Vi monomer was variable. Peptide doses of 0.1–2.0 μg injected per mouse as sugar-peptide conjugate were shown to be most effective.

TABLE 4

Serum Antibody Response of Female BALB/c Mice Injected with Vi or Vi-Peptide Conjugate

| | | Vi Antibody | | |
|---|---|---|---|---|
| Vaccine | Dose Vi mg | 12 d after 1st Immuniz. mg/ml | 24 d after 1st Immuniz. mg/ml | 12 d after 2nd Immuniz. mg/ml |
| Vi | 0.25 | 0.194 | 0.005 | 0.053 |
| Vi-Pep 278h | 0.25 | 0.049 (0.000–0.078) | 1.455 (0.296–1.906) | 2.959 (1.533–3.148) |
| BALB/c PBS | — | 0.223 | 0.205 | 0.233 |

Female BALB/c mice 2–3 months old were injected subcutaneously 2 weeks apart with 0.2 ml of each vaccine in IFA. There were 5 mice for each experimental group. Twelve and 24 days after the first and 12 days after the second immunization were exsanguinated and their sera were assayed for Vi antibodies by ELISA as described in Material & Methods. Results are expressed as the geometric mean; in brackets the variation of the Vi antibody concentration in each group.

Example 2
Immunological characteristics of Vi and Vi-conjugates.

2.1 Antigenicity of native Vi. To test the antibody response induced by Vi, 2-3 month old female BALB/c (four-five mice per group) were injected subcutaneously (sc) with varying doses of the Vi-antigen alone in Incomplete Freund's Adjuvant (IFA) 2 weeks apart. Mice were exsanguinated 12 and 24 days after the first and 12 days after the second immunization. Sera of all mice belonging to one group were pooled. Anti-Vi antibodies were measured by ELISA as described in Material & Methods herein and specific antibody levels expressed as Absorbance$_{405}$ (A$_{405}$).

Figure 1A:
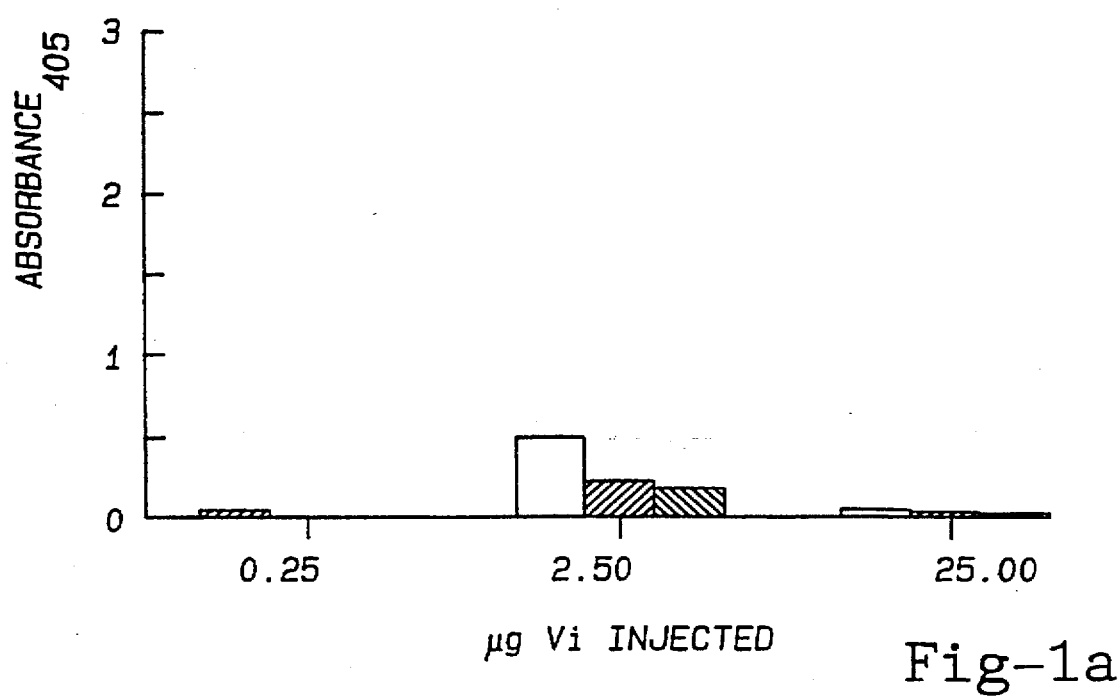

As shown in FIGS. 1–1a, one injection of Vi elicited a Vi antibody response in the mice. Reinjection of Vi did not induce a booster effect, as expected for T-ind antigens. Subcutaneous immunization with 2.5 µg Vi per mouse in IFA gave the strongest specific antibody production; a higher dosage did not result in an enhanced immune response.

The Vi-preparation used in this experiment contained residual amounts of protein (<1%). The relatively high Vi-immune response might be explained by this fact.

2.2 Antigenicity of Vi-conjugates.

2.2.1. Relation to injected antigen dosage. The effect of different doses on the immunogenicity of native and conjugated forms of Vi was studied. Anti-Vi antibody response was induced in mice by injection of 2.5 µg or 0.25 pg of Vi alone or of Vi-conjugates Vi-Pep II, Vi-Pep278h, Vi-Pep348h comprising 2.5 µg or 0.25 µg Vi. Four female BALB/c mice per group were immunized sc with 2.5 µg Vi alone or as a conjugate in IFA 2 weeks apart (for injected amounts of peptide as conjugate see Table 3). The anti-Vi antibody response was measured by ELISA and the magnitude of specific immune response is depicted in FIGS. 2a–f as A$_{405}$. Each panel shows geometric means of the sera obtained from 4 individual mice injected with the same antigen. Pooled sera of 4 mice immunized with Vi alone or with PBS in IFA respectively served as controls.

Figure 2A:
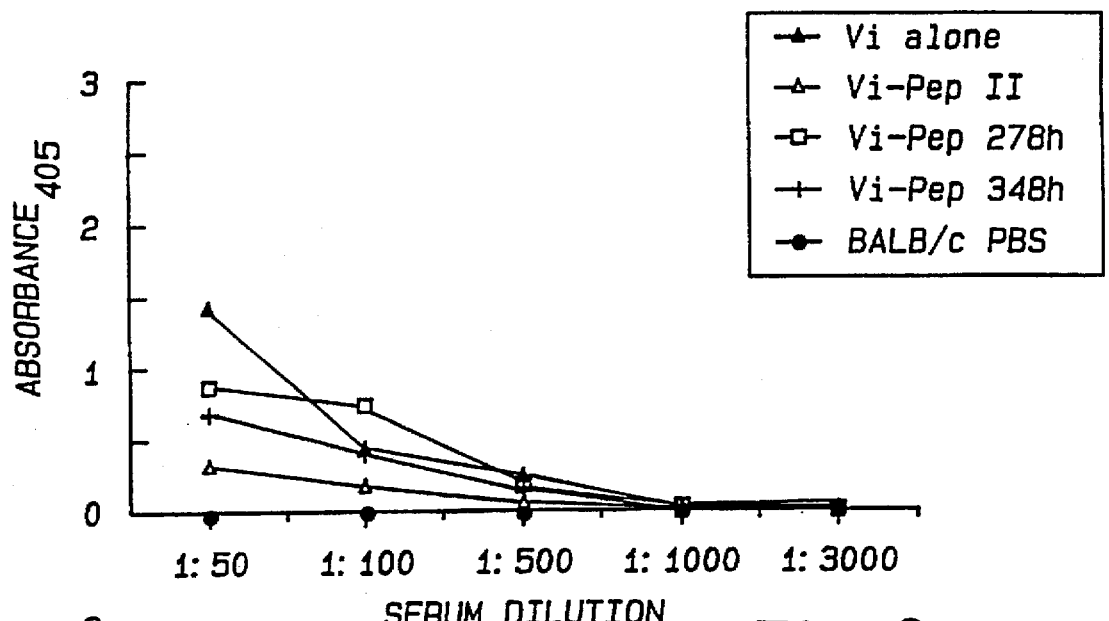
FIGS. 2a–f show anti-Vi antibody response induced in mice by Vi alone or Vi-conjugates Vi-Pep II, Vi-Pep278h and Vi-Pep348h ((a–c) 2.5 µg and (d–f) 0.25 µg Vi injected per mouse), 12 (a and d) and 24 days (b and e) after first immunization and 12 days after second immunization (c and f).
Figure 2B:
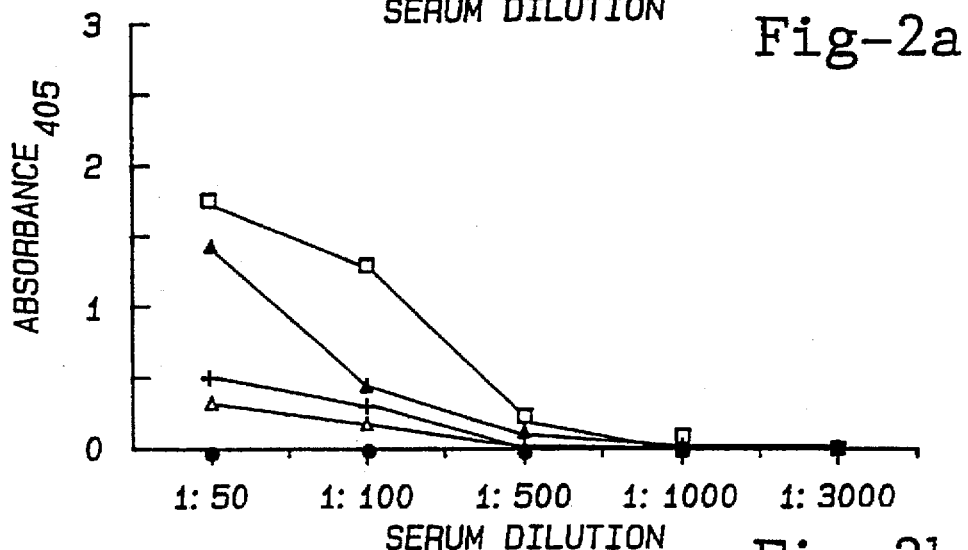
Figure 2C:
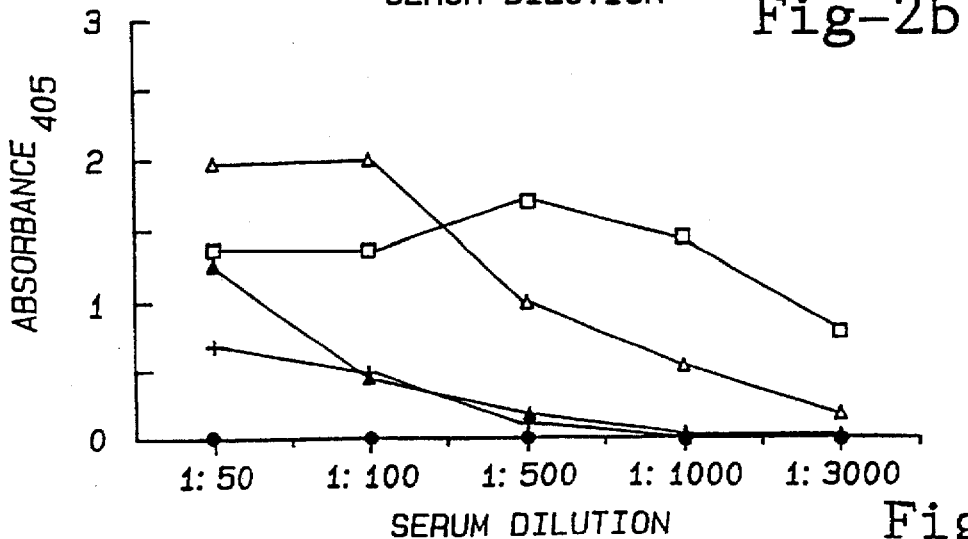

The results presented in FIGS. 2a–f show that twelve days after the first injection of 2.5 µg Vi alone or as conjugate (for the corresponding injected peptide amounts see Table 3b), all of the Vi-peptide conjugates showed anti-Vi immune responses lower than that elicited by Vi in its native form (FIG. 2a). Monitoring the Vi antibody levels for an additional period of 12 days without renewed immunization, indicated a clear increase of Vi specific antibodies in mice injected with Vi-Pep278h (FIG. 2b). Reinjection elicited a definite booster response upon immunization with Vi-Pep II and Vi-Pep278h, respectively, but not with vi alone (FIG. 2c).

Figure 2D:
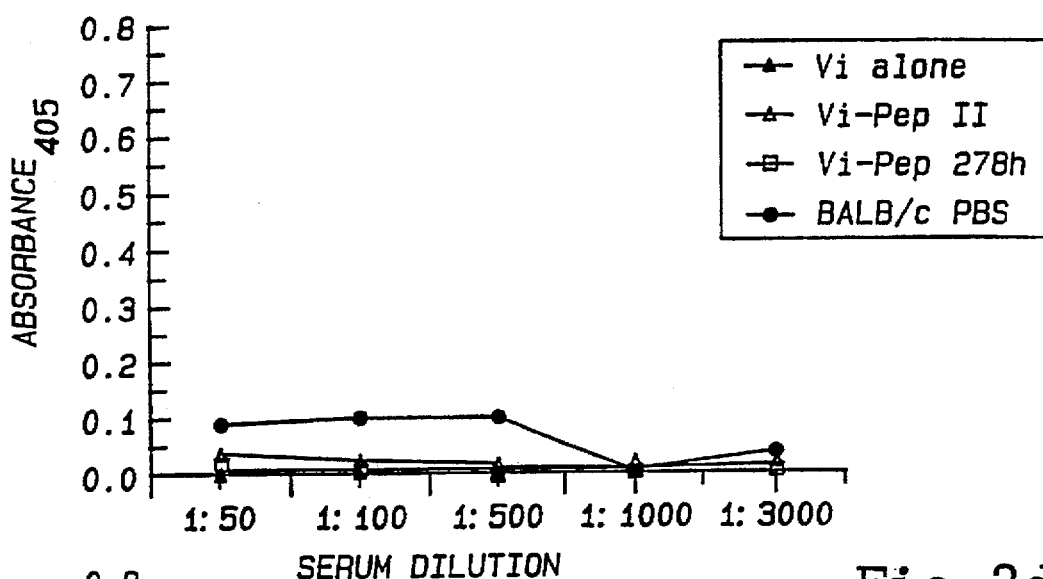
Figure 2E:
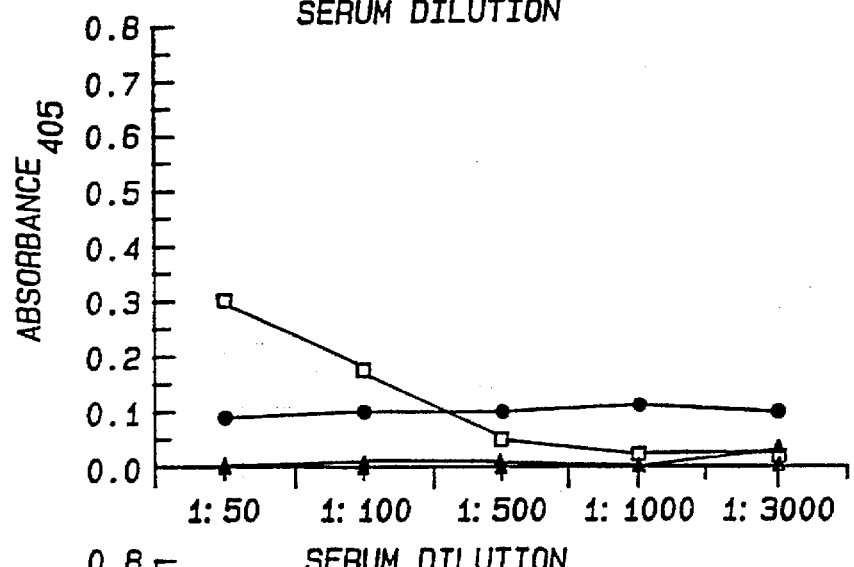
Figure 2F:
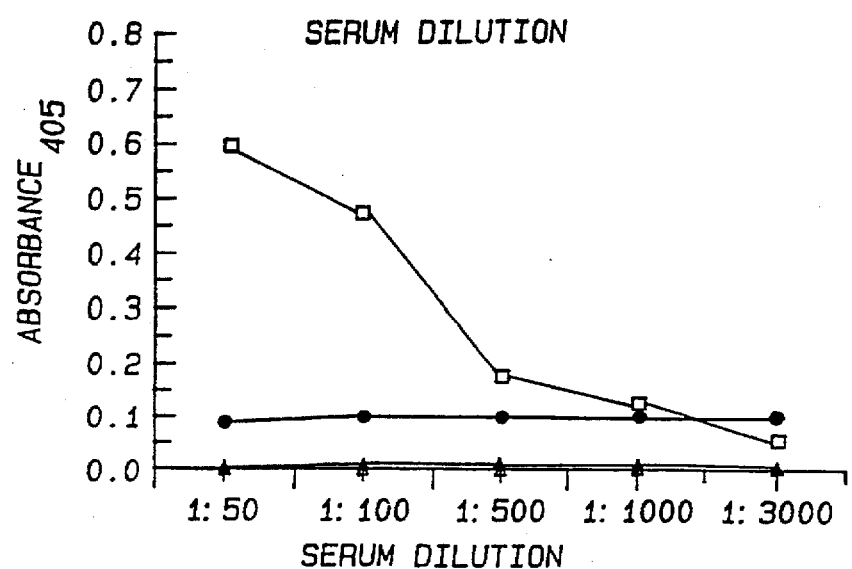

Lowering the dose of injected Vi to 0.25 µg per mouse (for corresponding injected peptide amount, see Table 3a) resulted in only minor Vi antibody levels induced by Vi alone and Vi-Pep II (FIGS. 2d–f). In contrast, the immune response elicited by the Vi-pep278h conjugate showed, upon a second immunization, a clear booster effect (FIG. 2f). Interestingly, it should be noted that the injected peptide amount in this conjugate was only 0.17 µg per animal (see Table 3a).

2.2.2. The kinetics of anti-Vi antibody production induced by Vi and Vi-conjugates in mice immunized as described above was studied. Anti-Vi antibody levels higher than induced by Vi alone are regarded as positive values, anti-Vi antibody levels lower than induced by Vi alone are regarded as negative values. Sera were assayed for Vi antibodies by ELISA. Results are expressed in FIGS. 3a, 3ab, 3b, and 3bb as A$_{405}$ and show the geometric means ±SD obtained by sera of 4 mice injected per antigen.

FIGS. 3a, 3ab, 3b, and 3bb illustrate the development of Vi antibody production upon two successive injections of Vi and Vi-conjugates in two different antigen doses. FIG. 3a: 2.5 µg Vi injected per mouse of Vi-Pep II, Vi-Pep278h, Vi-Ova, Vi-Pep348 and Vi-CRP 77–83; FIG. 3b): 0.25 µg Vi injected per mouse of Vi-Pep II and Vi-Pep278h. FIGS. 3ab, and 3bb–for comparison, Vi antibody levels induced by 2.5 µg Vi alone. As Shown in FIG. 3a, twelve days after the first immunization, all of the conjugates induced clearly lower Vi antibody levels than elicited by Vi alone, although the same amount of Vi was injected. After a "lag"-phase of about 12 days, the sera of animals immunized with Vi-conjugates expressed a marked increase in the specific Vi antibody level. This effect is specially evident for conjugate Vi-Pep278h in both applied doses (FIGS. 3a and 3b). Reinjection after 24 days triggered a booster response typical for T-dep antigens (for comparison see FIGS. 3ab and 3bb). Vi-Pep II, Vi-Pep278h and Vi-Ova induced higher Vi antibody levels than elicited by injection of Vi alone. Notably, the conjugate Vi-Pep278h gave rise to a stronger anti-Vi immune response than the Vi-protein conjugate Vi-Ova (FIG. 3a).

Immunization with a tenfold lower antigen dose emphasized the described effect of Vi antibody production induced by Vi-Pep278h (FIG. 3b).

Vi antibody concentrations elicited in mice by the Vi-Pep278h conjugate are given in Table 4. The specific antibody level induced by Vi-Pep278h showed a 30-fold increase from day 13 to day 24 after the first immunization. Reinjection resulted in doubling of the Vi antibody concentration to about 3 µg/ml, 55-fold higher than elicited by Vi alone.

2.2.3. Anti-Vi antibody specificity. The immune response to T-dep antigens is characterized by the formation of germinal centers, which have been associated with the concept of immunological memory. They are believed to provide a particular microenvironment allowing B cells to undergo V gene hypermutation to express antibodies with higher affinity receptors and altered isotype distribution.

Figure 4A:
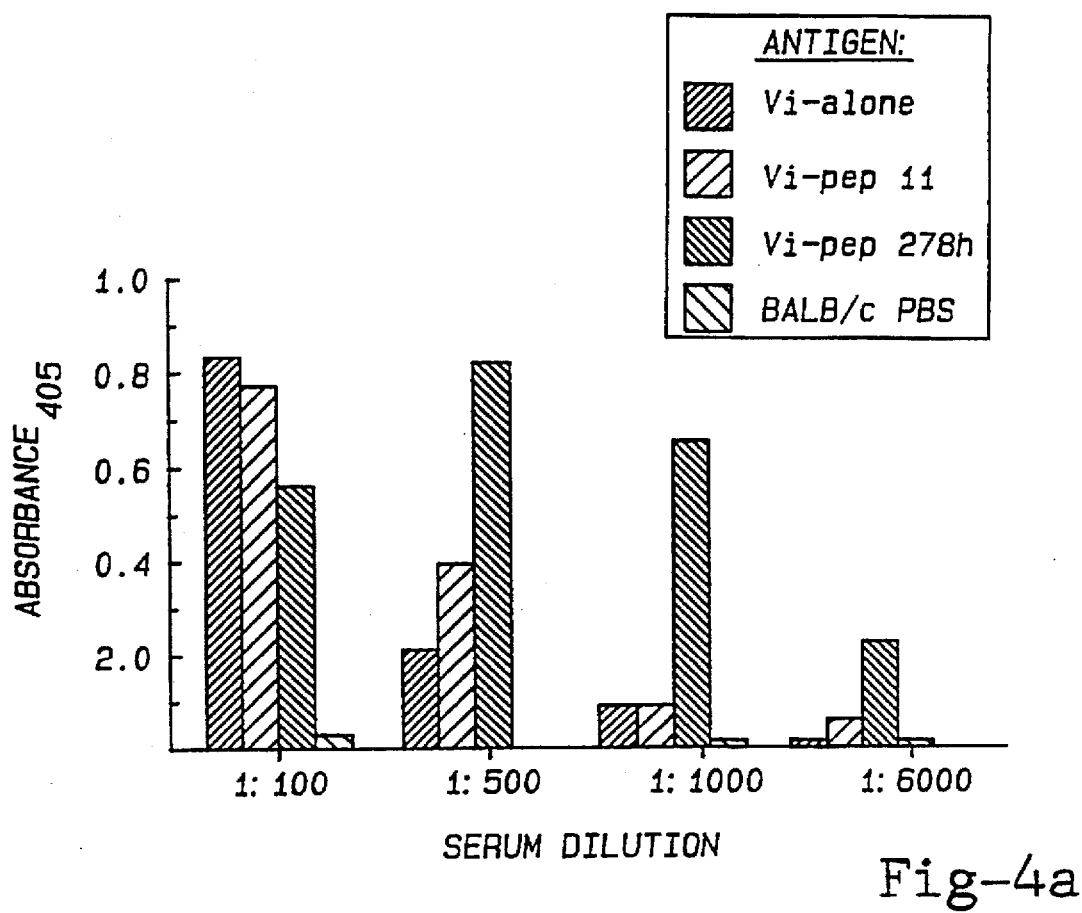
FIGS. 4a–b show the specificity of anti-vi antibodies elicited in mice immunized with Vi alone or with conjugates Vi-Pep II and Vi-Pep278h. The antibodies were determined in ELISA plates coated with 2.5 µg (FIG. 4a) or 1.25 µg Vi per well (FIG. 4b).
Figure 4B:
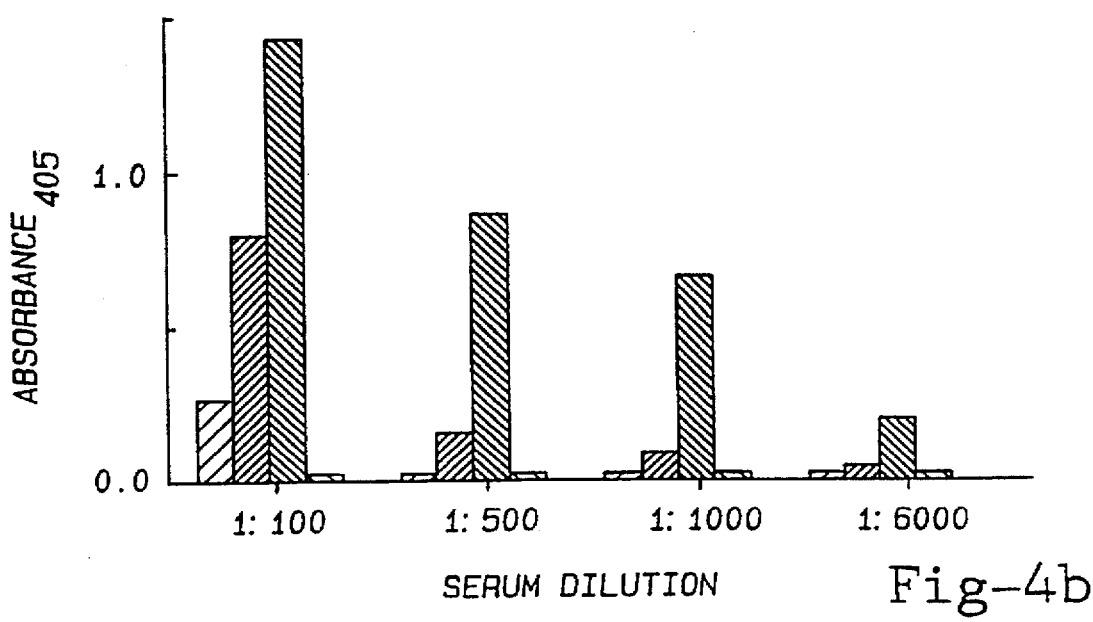

To test if Vi-specific B cells induced by Vi-peptide conjugates undergo this maturation process, the specificity of Vi antibodies elicited by Vi in native and conjugated forms was compared. Four-five female BALB/c mice were immunized with the antigens Vi, Vi-Pep II and Vi-Pep278h (sc) in IFA, each containing 2.5 µg Vi either alone or as conjugate. Animals were exsanguinated 12 days after the second injection and Vi antibodies determined by ELISA. The symbols in FIGS. 4a–b define individual representative mice of each group. ELISA plates were coated with 2.5 µg Vi per well FIG. 4a or with 1.25 µg Vi per well FIG. 4b; FIG. 4a shows that the Vi specific antibody titers induced by Vi alone are lower than induced by Vi-Pep278. Reducing the antigen amount coated to the ELISA plate (FIG. 4b) reveals an even clearer picture. Vi antibodies induced by Vi-peptide conjugates recognize at significant levels the decreased amount of Vi, whereas sera of mice immunized with the native Vi barely show any binding.

To further confirm T-dep characteristics of the Vi-peptide conjugates, the isotype distribution of elicited Vi antibodies in mice immunized as above with Vi- alone or Vi-Pep278h, was determined. IgM and IgG composition of anti-Vi antibodies in immunized mice was assayed by ELISA. Specific IgM antibodies, recognizing Vi, were detected by using goat anti-mouse Fab$_2$ IgM peroxidase conjugate (FIG. 5a), and specific IgG antibodies were detected by goat anti-mouse Fab$_2$ IgG alkaline phosphatase conjugate (FIG. 5b). Results are shown for single representative mice.

Figure 5A:
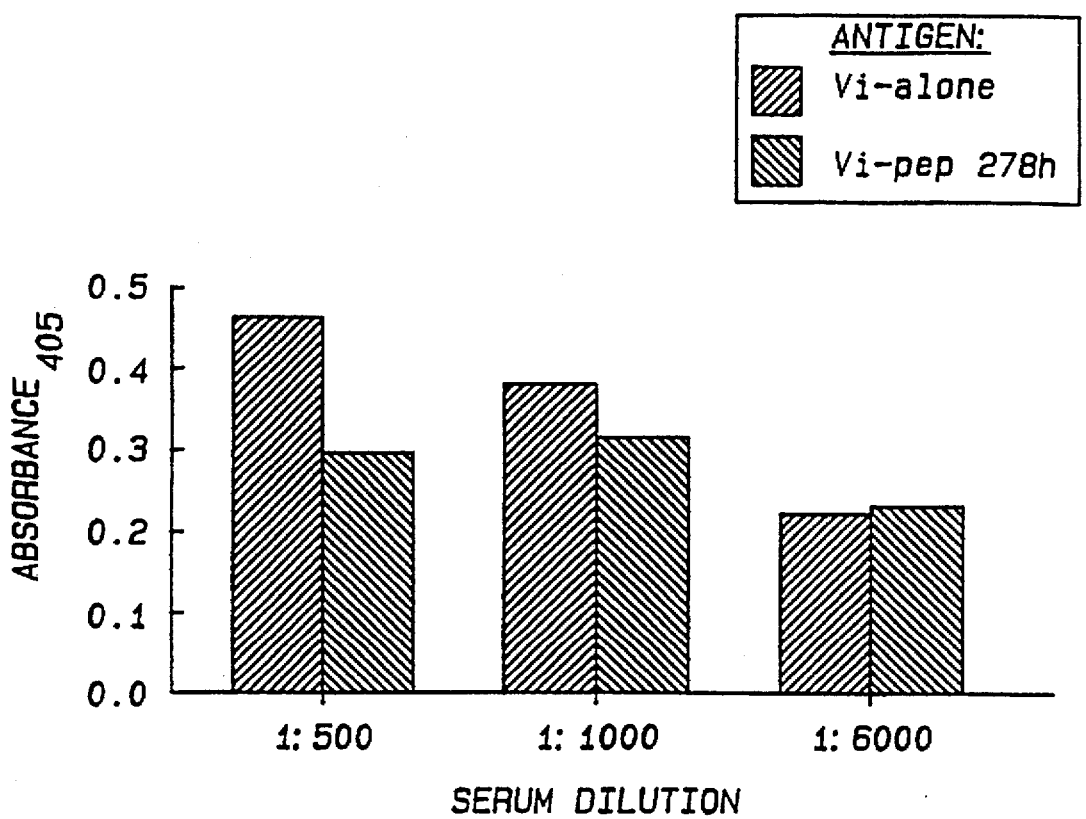
FIGS. 5a–b illustrate isotype characterization of anti-Vi antibodies elicited in mice by Vi alone or by conjugate Vi-Pep278h.
Figure 5B:
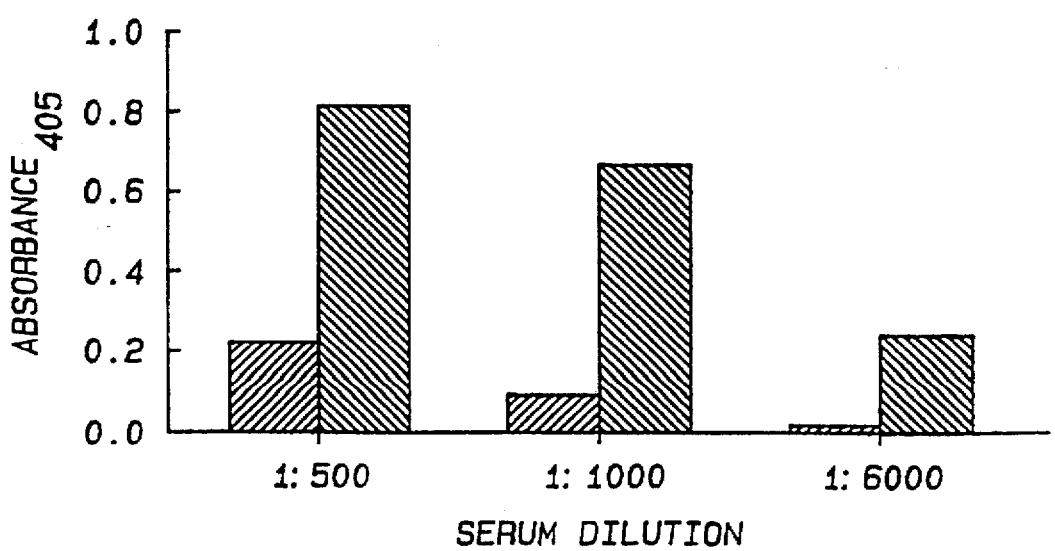

The isotype specificity of the anti-Vi sera obtained after repeated immunization is shown in FIG. 5a–b. Antibodies to the native Vi molecule seem to be mainly restricted to the IgM isotype class, whereas the Vi-Pep278 conjugate elicited in addition a clear IgG antibody response to the Vi antigen, indicating that coupling a selected T cell epitope (in this case peptide 278h) to a T-ind antigen, like Vi, results in the isotype class switch of a Vi-specific B cell population, typically observed for T-dep antigens.

In order to follow up long-term anti-Vi antibody production, animals were immunized for a third time and the specific immune response monitored over a time period of 72 days. Groups of 4–5 female BALB/c mice were injected sc with the Vi alone, Vi-Pep II and Vi-Pep278h antigens in IFA at the time points indicated in FIG. 6a–b. The immune response was monitored over a time period of 108 days (72 days after the last immunization) by determining the Vi antibody level in the different sera by ELISA. Obtained results are expressed as the geometric means and are shown at a serum dilution of 1:100 (panel A) and 1:1000 FIG. 6b. No booster effect could be observed after this additional injection of Vi-peptide conjugates Vi-Pep II and Vi-Pep278h. Anti- Vi levels induced by the conjugates were higher than those elicited by Vi alone, and did not decrease 2½ months (FIG. 6) and even 6 months (data not shown) after the last injection.

2.2.4. Effect of adjuvant and immunization mode on anti-Vi antibody production induced by Vi-Pep II. To test the influence of adjuvant on Vi-specific antibody formation by native and modified Vi, the antigens were either injected subcutaneously in IFA or PBS. Vi-Pep II conjugate was prepared in IFA and in PBS. One group of 4 mice was injected sc FIGS. 7aa, 7ba, and 7ca and a second group im FIGS. 7ab, 7bb, and 7cb with each antigen preparation, (2.5 μg Vi injected per mouse). Sera were obtained at 12 FIG. 7aa and 7ab and 24 days FIG. 7ba and 7bb after first immunization and 12 days after second immunization FIGS. 7ca and 7cb. Anti-Vi antibodies were measured by ELISA, shown as $A_{405}$ and giving the means ±SD. The results presented in FIGS. 7aa, 7ba, 7ca indicate that IFA is necessary to express the kinetics of a T-dep immune response.

Figure 7A:
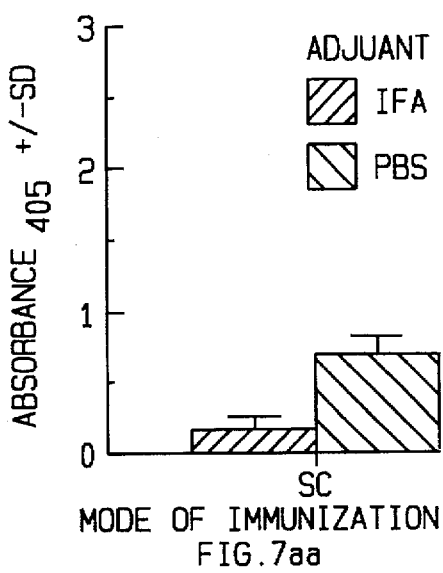
FIGS. 7aa, 7ab, 7ba, 7bb, 7ca and 7cb show effect of adjuvant and immunization mode on anti-Vi antibody production induced by Vi-Pep II injected (FIGS. 7aa, 7ba, and 7ca) subcutaneously (sc) or (B) intramuscularly (im) in mice, 12 (FIGS. 7aa and 7ab) and 24 days (FIGS. 7ba and 7bb) after first immunization and 12 days after second immunization (FIGS. 7ca and 7cb).
Figure 7A:
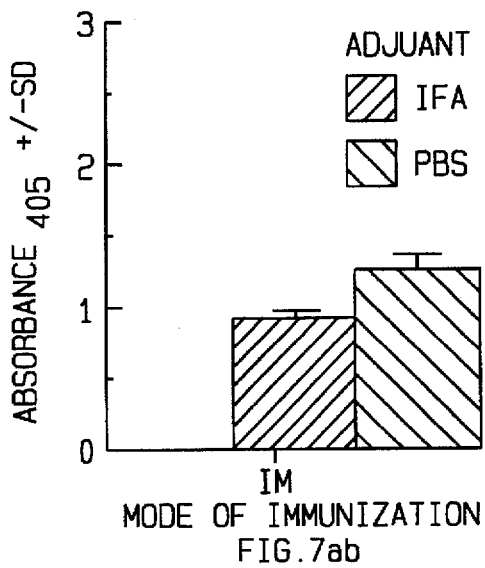
Figure 7B:
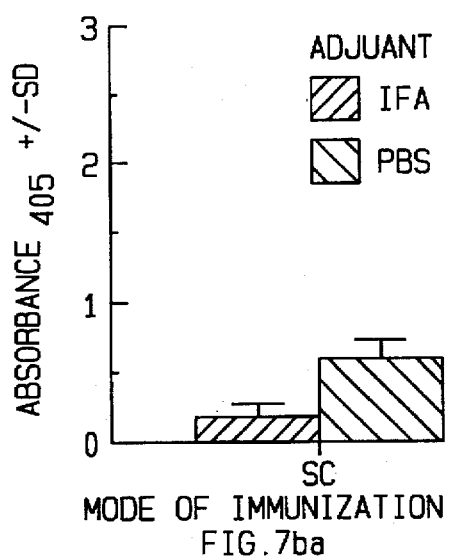
Figure 7B:
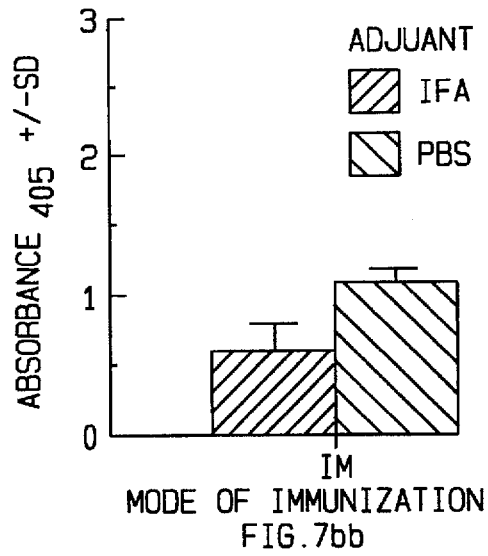
Figure 7C:
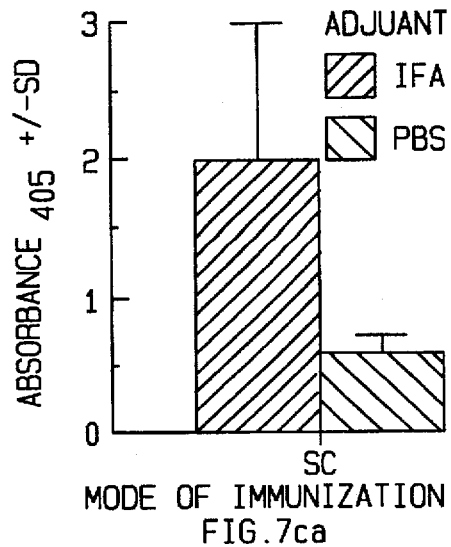
Figure 7C:
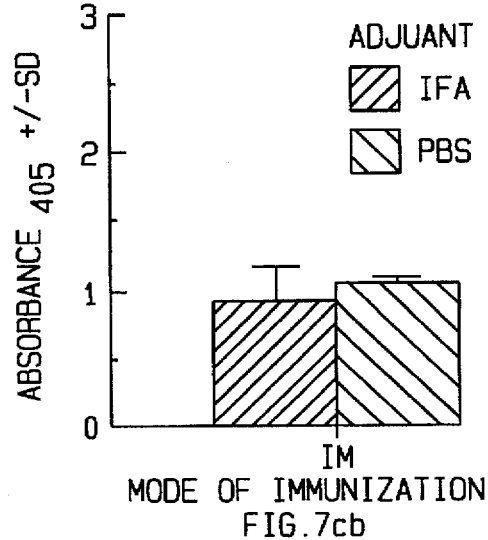

Changing the immunization mode by administering Vi intramuscularly (i m), illustrates 2 facts (as shown in FIGS. 7ab, 7bb, and 7ca). First, intramuscular delivery of the Vi-conjugate leads to a higher primary Vi immune response than elicited by subcutaneous administration of the same antigen preparation. Secondly, this injection route does not result in a booster effect, as observed for the subcutaneous immunization. The same trend was observed by injecting Vi-pep II in PBS, either subcutaneously or intramuscularly FIGS. 7aa, 7ab, 7ba, 7bb, 7ca, and 7cb.

In further experiments with mice immunized with the conjugate Vi-278h in IFA, PBS or CFA (complete Freund's adjuvant), comparable titers of anti-Vi antibodies were obtained with the three adjuvants (data not shown).

2.2.5. Anti-Vi antibody production induced by free peptide II mixed with Vi before immunization. In order to evaluate the necessity of covalently binding Vi to peptide epitopes before immunization, Vi and Pep II were physically mixed and injected subcutaneously in IFA to a group of female BALB/c mice, and compared to immunization with conjugate Vi-Pep II. Both antigen preparations were injected sc to groups of 4 mice in IFA (the mixture of Pep II and Vi was injected in 1 syringe). The animals were bled 12 and 24 days after the first FIGS. 8a and 8b, respectively) and 12 days after the second immunization (FIG. 8c). Anti-Vi antibodies were determined by ELISA and the results shown as $A_{405}$. Each curve presents the geometric means ±SD.

Figure 8A:
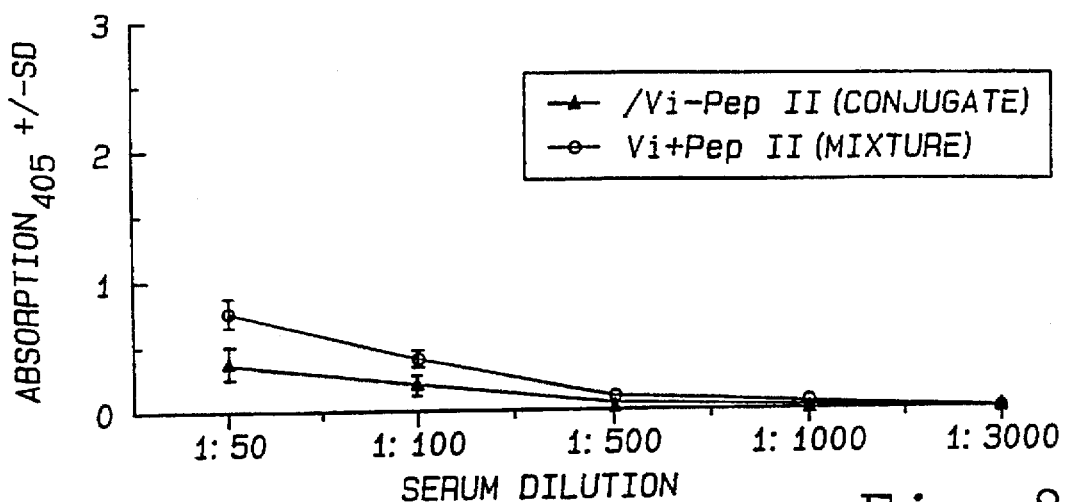
FIGS. 8a–c show anti-Vi antibody production induced in mice by Vi-Pep II conjugate or by free Pep II mixed with Vi before immunization, 12 (FIG. 8a) and 24 days (FIG. 8b) after first immunization and 12 days (FIG. 8c) after second immunization.
Figure 8B:
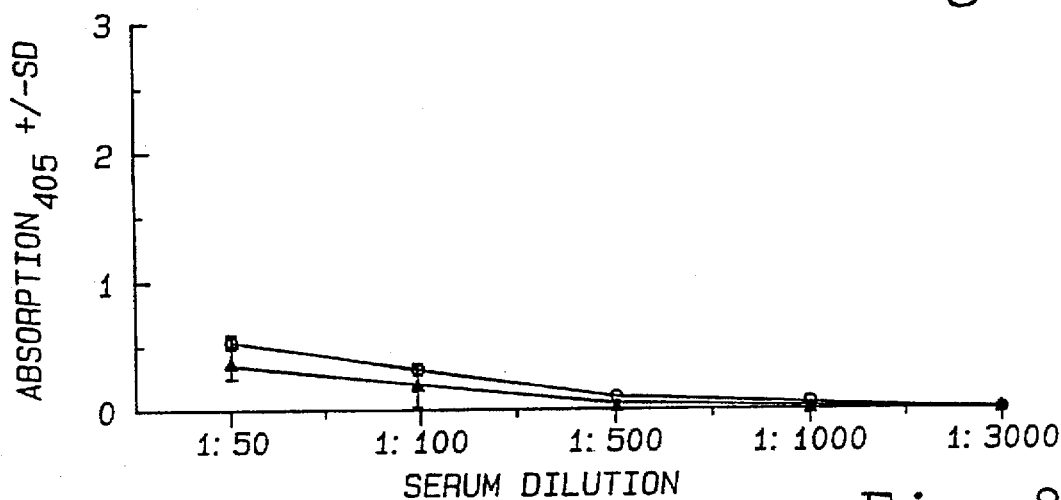
Figure 8C:
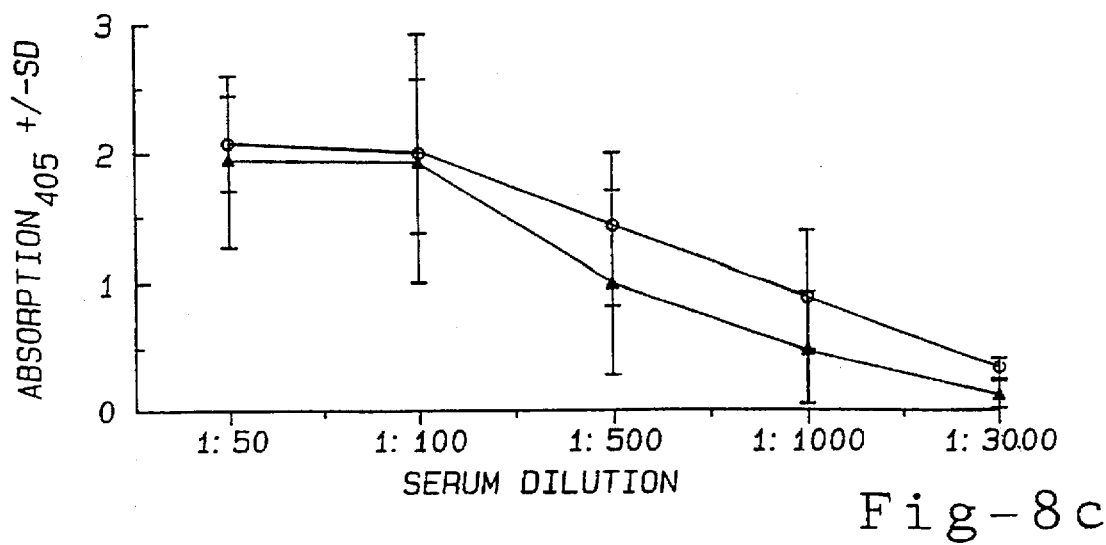

As shown in FIGS. 8a–c mixing vi and peptide II, resulted in exactly the same immune response as described for the Vi-Pep II conjugate. A first immunization only led to low Vi antibody levels, whereas reinjection gave rise to a clear booster effect.

Figure 9:
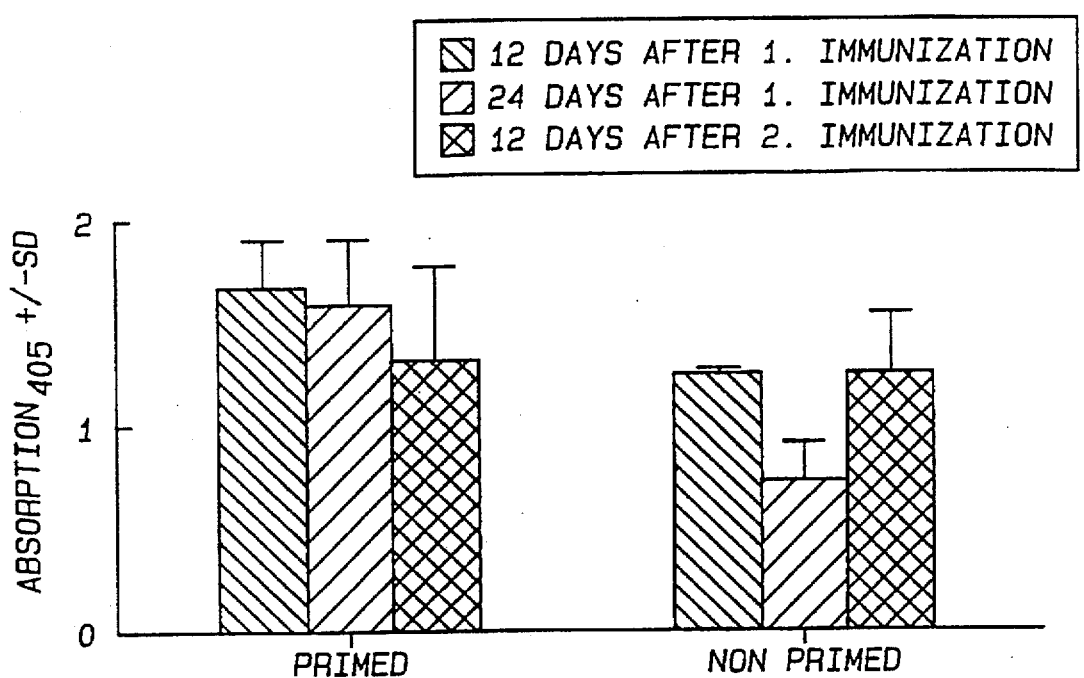
FIG. 9 shows effect of carrier priming on anti-Vi antibody production in mice immunized with conjugated Vi-Pep II, primed sc 14 days before immunization with free Pep II in IFA (left) or non-primed (right).

2.2.6. Effect of "carrier"-priming on anti-Vi antibody production. To test the effect of priming with free peptide on the polysaccharide response induced by Vi-peptide conjugates, a group of 4 female BALB/c mice was primed sc with 1 μg peptide II in IFA per animal. Two weeks later animals were injected with the Vi-Pep II conjugate, containing 2.5 μg Vi. Sera were taken at the time points indicated in FIG. 9 and analyzed by ELISA. Anti-polysaccharide antibody levels, as measured on the indicated time points, are shown in FIG. 9. Priming with a dose of 1 μg peptide II per mouse resulted in a stronger primary immune response to Vi in comparison to the antibody levels elicited in non-primed animals. Nevertheless, no effect of priming was observed concerning the secondary immune response.

Figure 10A:
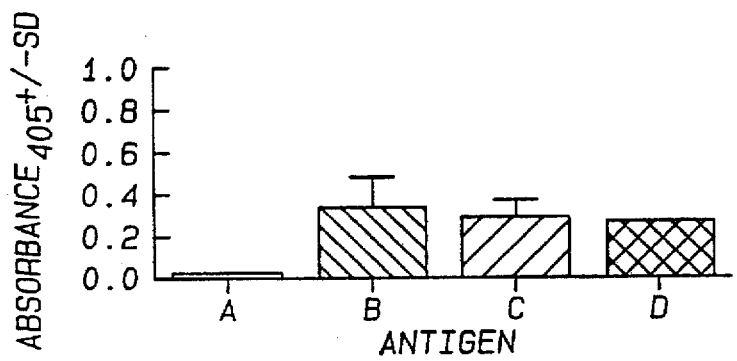
FIGS. 10a–d show the anti-Vi immune response induced in the same individual mouse by Vi-Pep277(S) (antigen A), Vi-Pep278h (antigen B, after mice were injected with Vi-Pep277(S)), Vi alone (antigen C, after mice were injected with Vi-Pep277(S)), and vi-Pep278h (antigen D), at serum dilution 1:50 (FIGS. 10a and 10b) and 1:1000 (FIGS. 10c and 10d), 12 days after first (panel A) and 12 days after second (FIGS. 10b and 10d) immunization.
Figure 10B:
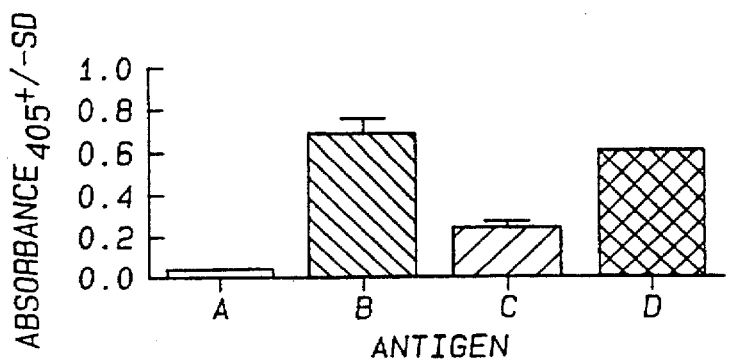
Figure 10C:
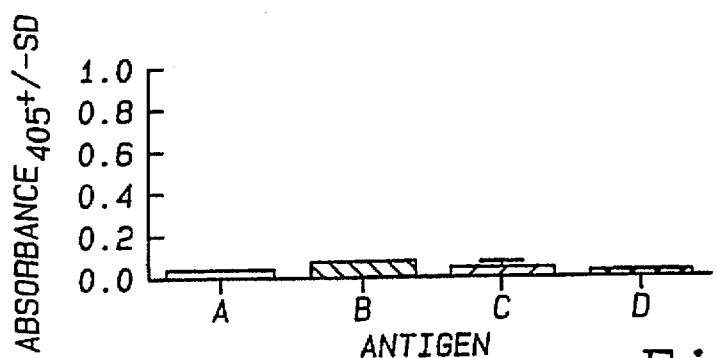
Figure 10D:
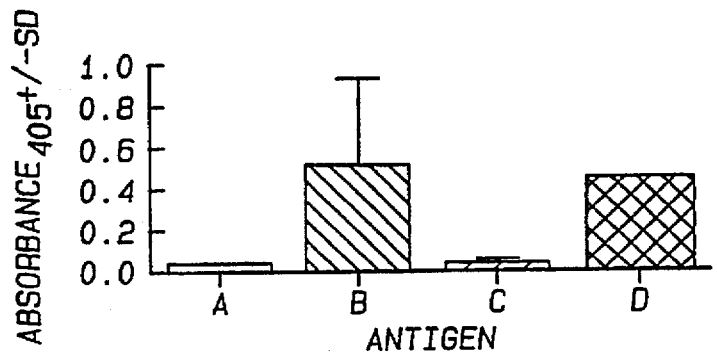

2.2.7. An anti-Vi immune response can be induced by Vi-Pep278h but not by Vi-Pep277(S) in the same, individual mouse. A group of 4 female BALB/c mice was injected sc with Vi-Pep277(S) in IFA 2 weeks apart (Vi content in the conjugate injected to each mouse 2.5 μg). The anti-Vi immune response was determined 12 days after the first (FIGS. 10a and 10c) and 12 days after the second injection by ELISA (FIGS. 10b and 10d). Two of these animals were reinjected with Vi-Pep278h, the other 2 with Vi alone (2.5 μg Vi alone or as conjugate). Again, the mice were bled 12 days after the first and second immunization and the Vi antibody levels were determined. For comparison, the immune response induced in animals which were injected with Vi-Pep278h only, is just delineated in the same figure. Results are expressed as $A_{405}$ and presented in 2 different serum dilutions, 1:50 (FIGS. 10a and 10b) and 1:1000 (FIGS. 10c, and 10d). The data show geometric means ±SD. Antigen A=Vi-Pep 277(S), Antigen B=Vi-Pep278h (after mice were injected with Vi-Pep277(S)), Antigen C=Vi alone (after mice were injected with Vi-Pep277(S)), Antigen D=Vi-Pep278h.

As shown in FIGS. 10a–d, immunization of female BALB/c mice with Vi-Pep277(S) did not result in a detectable Vi antibody response (Antigen A). To examine if the non-responsiveness could be attributed to the individual mice or to characteristics residing in the specific conjugate, the same mice which did not react to Vi-Pep277(S) were immunized with Vi-Pep278h (Antigen B) or the native Vi (Antigen C), respectively. Reinjection with Vi-Pep278h could definitively enhance the Vi antibody levels as- was shown for mice only injected with Vi-Pep278h (Antigen D). Reinjection with Vi alone also augmented the Vi immune response, however, to a lesser extent than induced by the Vi-conjugate.

2.2.8. Recognition of Vi-peptide conjugates by various anti-Vi sera. Vi and Vi-peptide conjugates Vi-Pep II, Vi-Pep II*, VI-Pep278h and Vi-CRP77–83 were used as immunogens coated to ELISA plates and checked for recognition by sera obtained from animals immunized with the corresponding conjugate or with sera obtained from animals immunized with other Vi-conjugates. The amount of bound antibody was determined by ELISA and is expressed in FIGS. 11a–f as $A_{405}$. Standard anti-Vi serum Burro 260 (FIG. 11a) was applied in a serum dilution of 1:12000, the other sera (FIGS. 11b–f) were diluted 1:200.

Figure 11A:
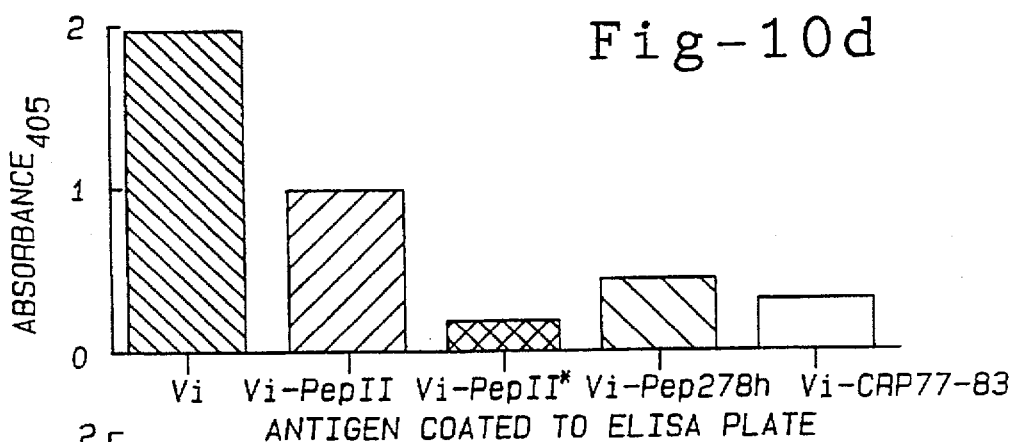
FIGS. 11a–f show screening of recognition of Vi alone (FIG. 11b) and of conjugates Vi-Pep II (FIG. 11c), Vi-Pep278h (FIG. 11d), Vi-Pep II* (FIG. 11e) and Vi-PCRP77–83 (FIG. 11f) coated to ELISA plates by the reference anti-Vi serum Burro 260 (FIG. 11a).
Figure 11B:
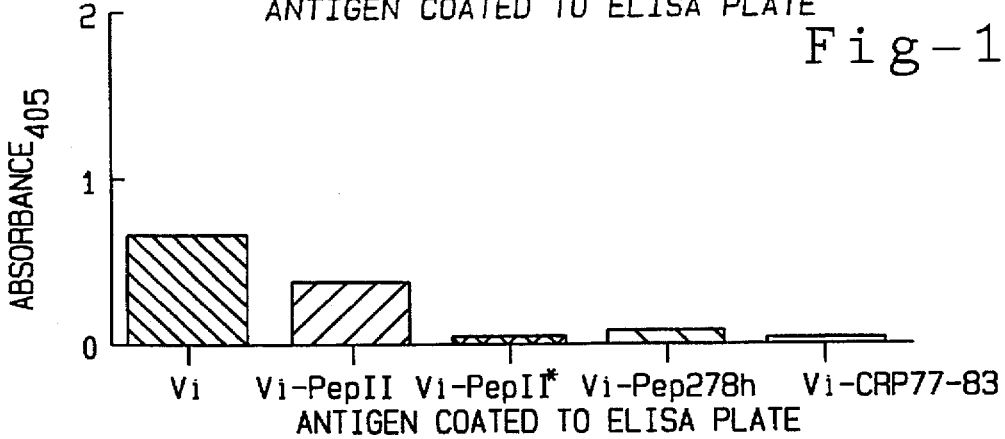
Figure 11C:
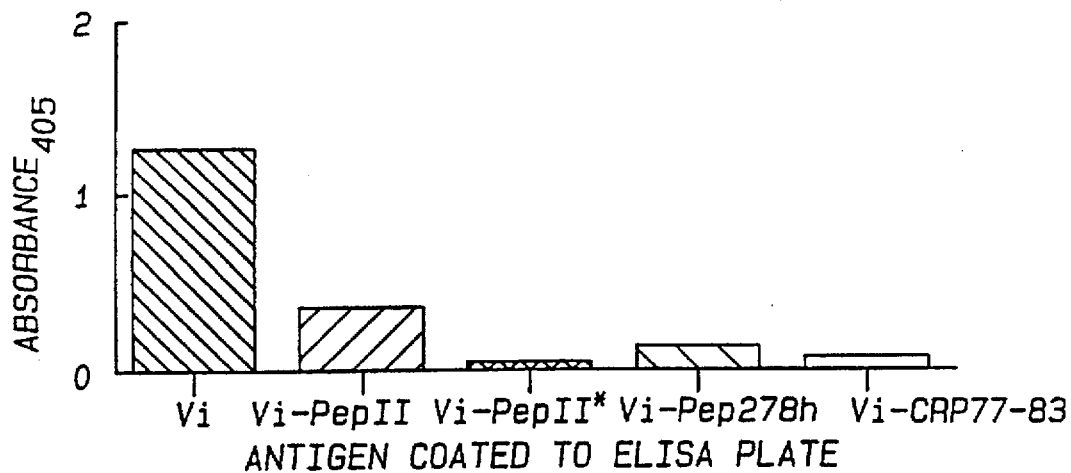
Figure 11D:
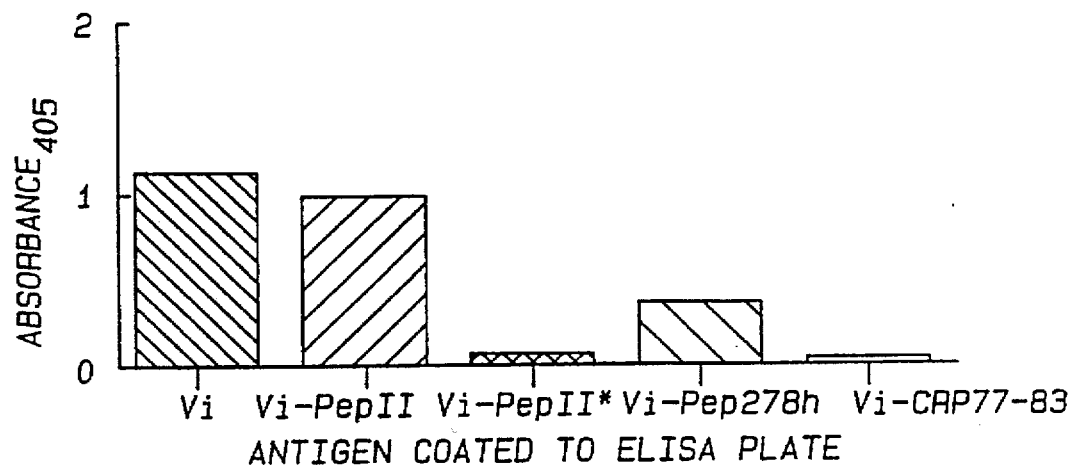
Figure 11E:
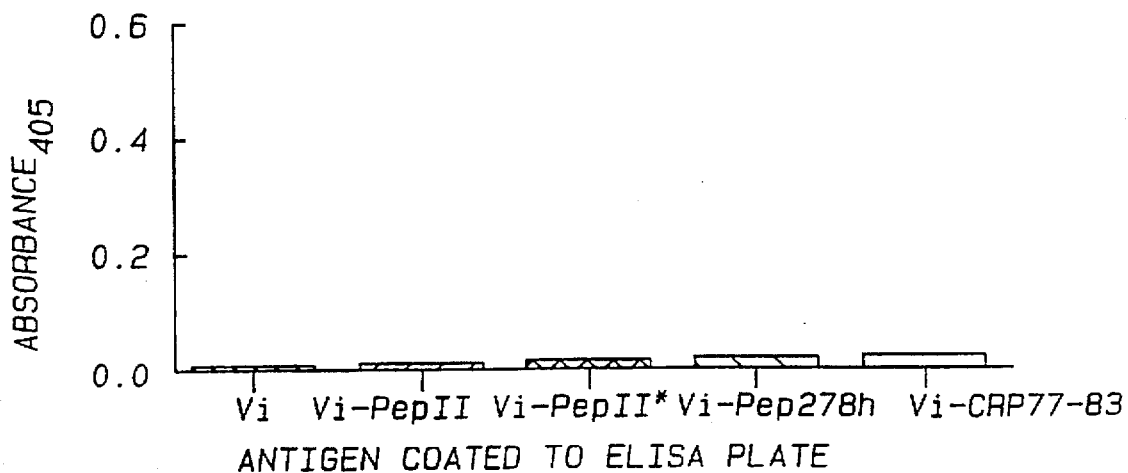
Figure 11F:
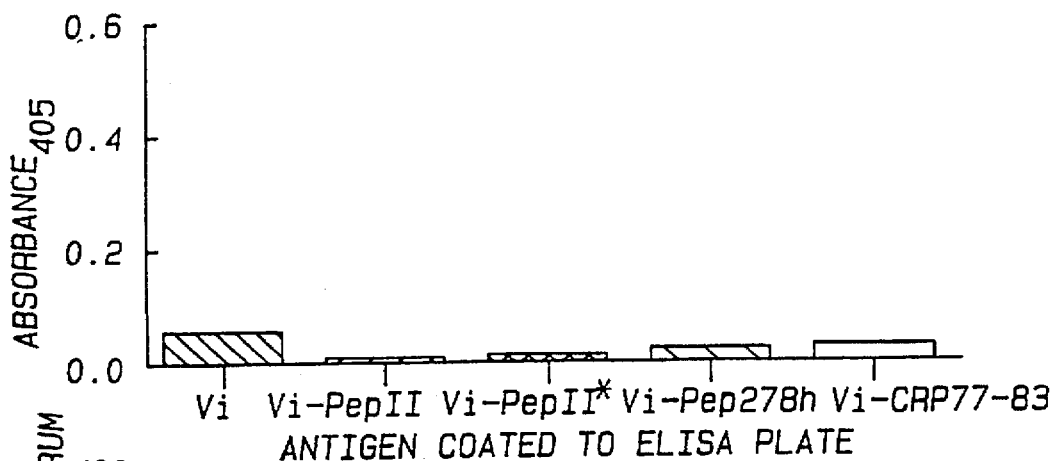
Figure 12A:
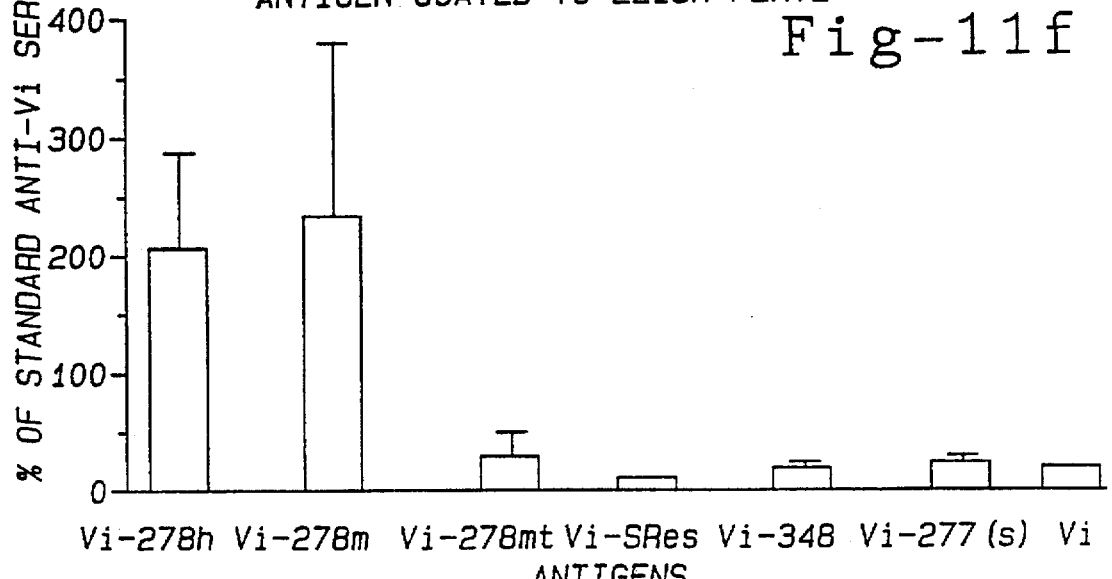
FIGS. 12a–e illustrate the immune response of different mouse strains to Vi and Vi-conjugates.
Figure 12B:
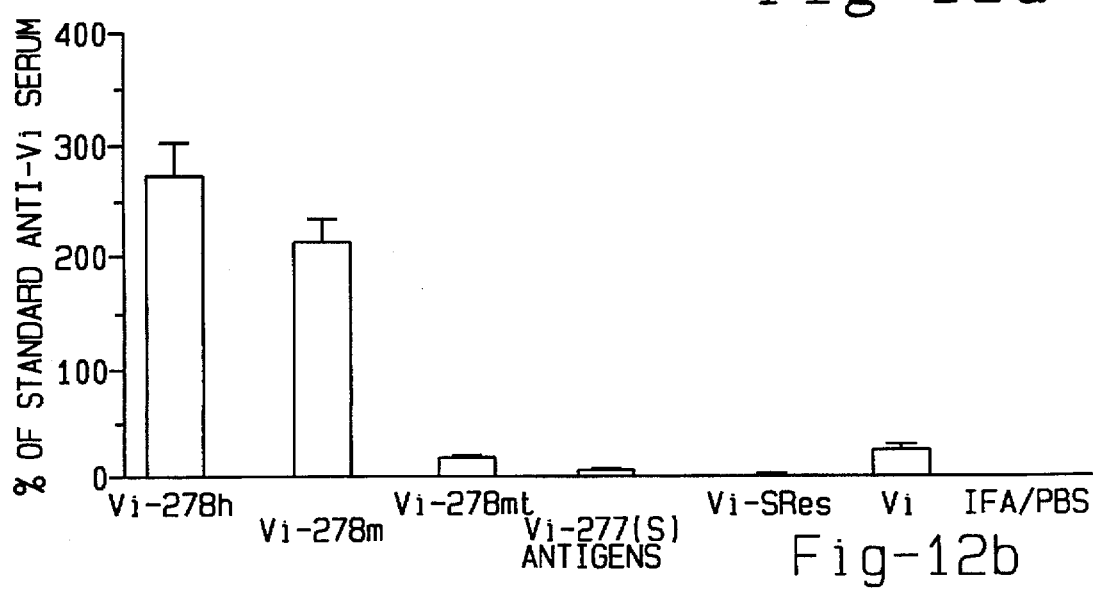
Figure 12C:
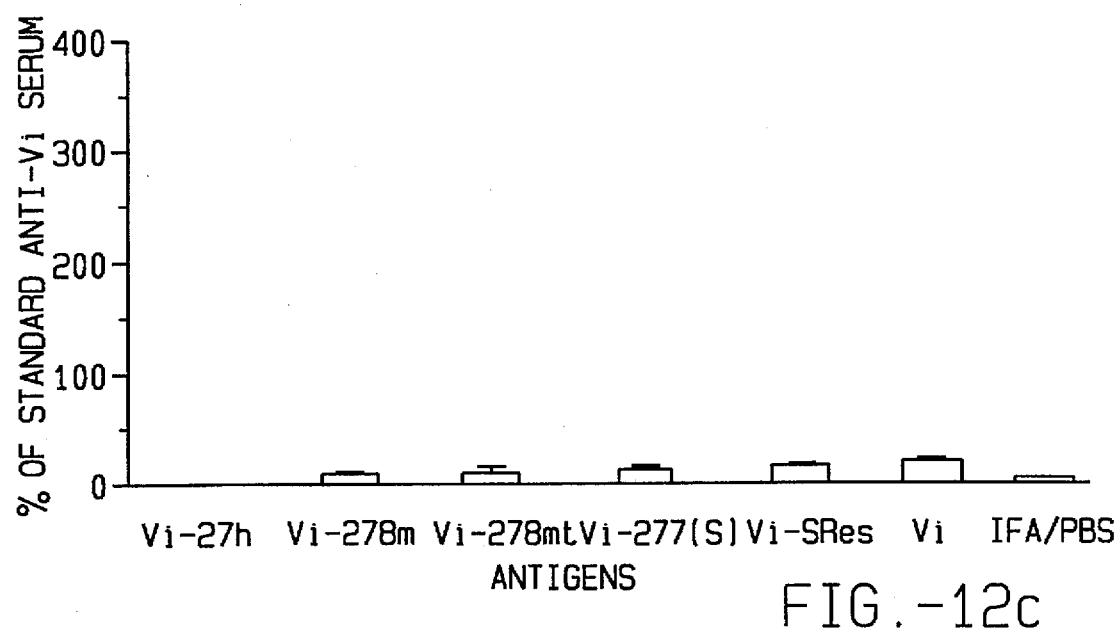
Figure 12D:
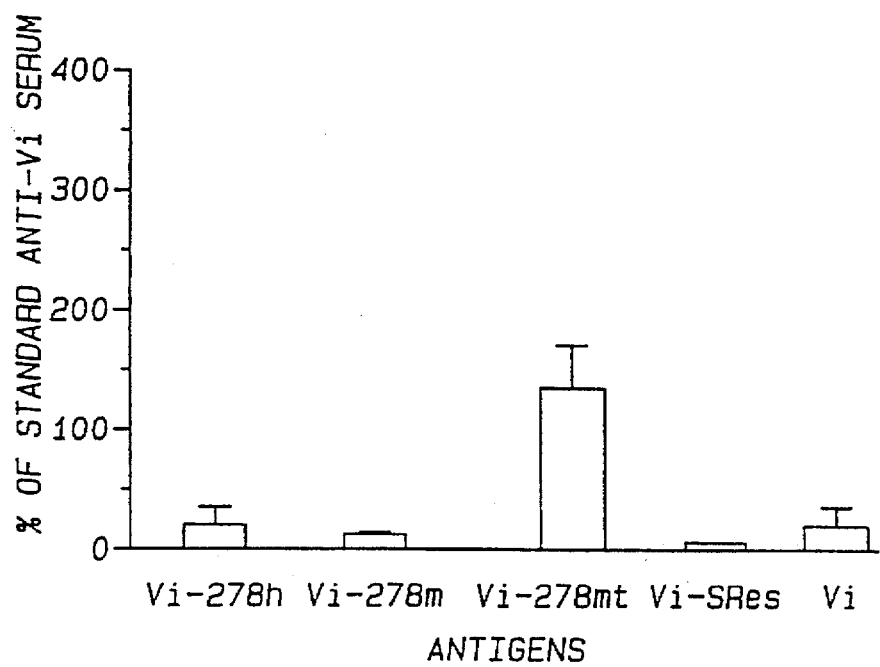
Figure 12E:
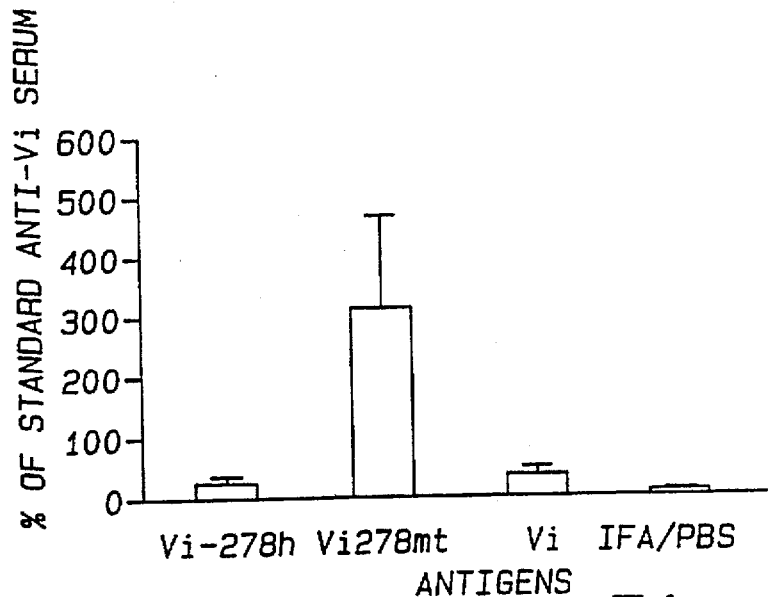

To analyze if coupling of peptides changed the antigenic structure of the Vi-moiety in the conjugate, the different Vi-conjugates as well as the native Vi were screened for recognition by the reference anti-vi serum Burro 260 FIG. 11a. Binding of peptide to Vi apparently influenced the antigenic activity of the Vi molecule, since all the conjugates showed in comparison to the native Vi, a reduced recognition by Burro 260 antiserum. No correlation was found to the peptide amount loaded onto the Vi molecule (see Table 2). Nevertheless, these results might partially explain the differences found in the antigenic activity expressed by distinct Vi-peptide conjugates. Vi-Pep II and Vi-Pep278h seem to bind higher amounts of Vi antibody contained within the Burro 260 antiserum than the less immunogenic conjugates Vi-PepII* and Vi-Pep CRP 77-83.

Characterization of the Vi antibodies induced by the different conjugates is shown in FIG. 11, panels B-F. Antisera induced by Vi-Pep II and Vi-Pep278h exhibited the highest cross-reactivity with the native Vi molecule but surprisingly only showed low recognition of the conjugate they were raised against. Antisera obtained after injection of Vi-Pep II* and Vi-Pep CRP 77-83 did not show any binding to the native Vi molecule or the presented conjugate antigens. Apart from the nature of the chosen peptide, these results indicate an influence of peptide load and coupling procedure on the immunogenic features of the Vi-peptide conjugate.

2.2.9. Immune responses to Vi-peptide conjugates in different mouse strains. In order to examine the immunogenicity of Vi-peptide conjugates in congenic mouse strains differing only in their MHC genes, BALB/c (H-$2^d$), BALB/k (H-$2^x$) and BALB/b (H-$2^b$) mice were immunized with Vi alone or with the conjugates Vi-278h, Vi-278m, Vi-278mt, Vi-277(S), Vi-SRes (Vi-SerRes). Five mice per group of each of the strains BALB/c, BALB/k, BALB/b, NOD and NON.NOD (FIGS. 12a–e, respectively) were injected sc with 2 µg Vi of the conjugates indicated in the figure, emulsified in IFA. After 4 weeks the mice obtained a boost of the same antigen dose and were exsanguinated 12 days later. Sera of individual mice were checked for Vi antibodies by ELISA. Specific antibody levels are expressed in FIGS. 12a–e as percentage of a standard anti-Vi serum (Burro 260).

The results in FIG. 12 indicate that the Vi-278h as well as the Vi-278m conjugate reaction is not limited to a certain MHC restriction. The peptides induced enhanced antibody titers against the sugar moiety of the conjugate both in BALB/c and in BALB/k mice. In contrast, BALB/b mice did not react to any of the injected conjugates. Thus, 2 of the 3 MHC genotypes were responders.

NOD and NON.NOD mice sharing the same MHC genes (H-$2^{NOD}$) show a different pattern of immunological reactivity to Vi-peptide conjugates. Only the mycobacterial 278mt homolog was able to give a Vi-specific helper effect.

2.2.10. IgG isotype distribution of anti-Vi sera. Five BALB/c mice per group were immunized sc with 2 µg Vi alone or with Vi-278h conjugate emulsified in IFA. Four weeks later the mice were boosted with the same antigen dose and were exsanguinated 12 days later. Individual serum samples were analyzed for antipolysaccharide IgG antibodies by the use of biotinylated rabbit anti-mouse subclass-specific antisera and streptavidin conjugated alkaline phosphatase by ELISA. Vi antibody levels are expressed as Absorbance $405^{nm}$ ($A_{405}$).

Examination of the subclass distribution of murine antibodies directed against the bacterial carbohydrate yielded the surprising observation that the carbohydrates alone stimulate IgG responses largely restricted to the rare IgG3 subclass. Carrier proteins like BSA or tetanus toxoid conjugated to bacterial capsular polysaccharides tend to induce anti-sugar antibody predominantly of the IgG1 isotype in mice.

Figure 13A:
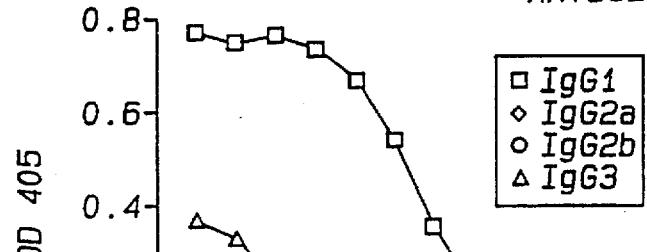
FIGS. 13a–c show the IgG isotype distribution of sera of mice immunized with Vi-278h conjugate emulsified in IFA, with Vi in IFA and with IFA/PBS, respectively.
Figure 13B:
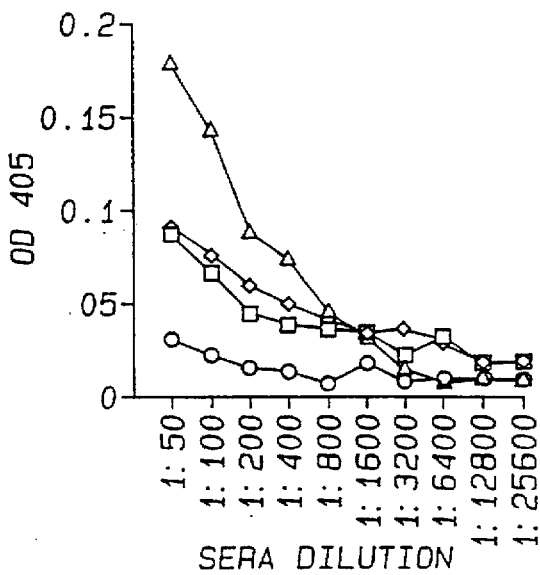
Figure 13C:
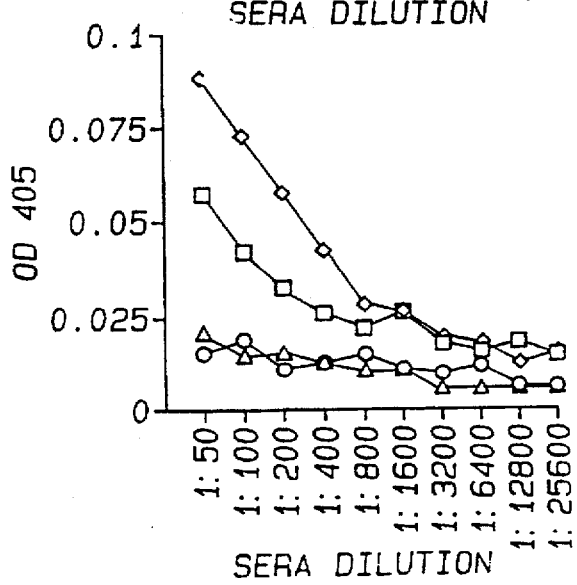

In order to examine the effect of peptide 278h conjugated to Vi, the IgG subclass distribution of anti-Vi sera was determined. As depicted in FIGS. 13a–c Vi injected alone elicited an immune response restricted mainly to the IgG3 subclass, whereas the peptide-sugar Vi-278h conjugate shifted the subclass distribution clearly to a IgG1 dominated one.

Conjugating the hsp65 peptide to a T-ind antigen therefore seems to be able to induce considerable qualitative changes in the immune response directed against the T-ind moiety of the complex.

Example 3

3.1. Antigenicity of Vi fragment-peptide conjugates. The immunogenicity of polysaccharides, including the Vi antigen, are related to their molecular sizes. Vi-fragments (about 45 kDa), prepared by ultrasonic cleavage, which does not alter the structure of its monomeric units and which produces a comparatively homogeneous polysaccharide, is less immunogenic than is the native Vi (about $3 \times 10^3$ kDa) (Szu et al, 1989). Five BALB/c mice per group were injected sc with 2 µg Vi fragments alone or as conjugate with peptide 278h emulsified in IFA. On day 12 after the boost serum samples were collected and tested for Vi fragment antibodies by ELISA. Specific antibody levels are expressed as percentage of a standard anti-Vi serum.

Figure 14:
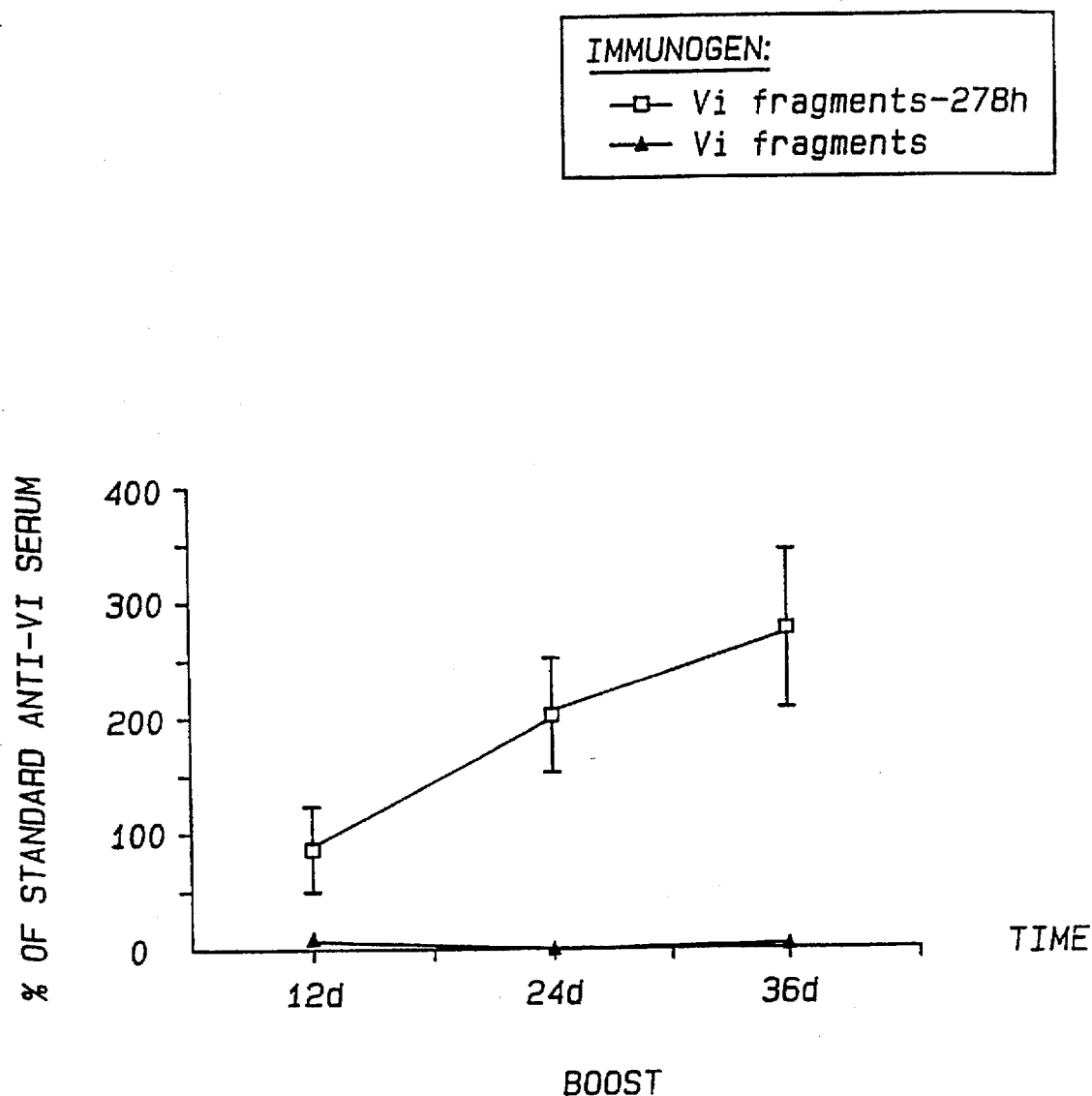
FIG. 14 shows the immune response of mice to Vi fragments and Vi fragments-278h conjugate.

As shown in FIG. 14, immunization of BALB/c mice with 2 µg of Vi-fragments alone did not result in any anti-Vi immune response. In contrast Vi-fragments conjugated to peptide 278h showed an enhanced antigenicity eliciting significant titers of anti-Vi antibodies.

Example 4

4.1. Antigenicity of Vi conjugated to homologs of peptide 278h. In order to determine if peptides derived from hsp65 representing self as well as foreign epitopes can function as T cell carriers for T-ind antigens in mice, we synthesized the peptides 278m and 278mt corresponding, respectively, to the mouse and the mycobacterial variants of the human 278 sequence (see Table 1) and conjugated them to Vi. Four BALB/c mice were injected sc with 2 µg of Vi alone or with Vi-278h, Vi-278m, Vi-278mtand Vi-SerRes conjugate emulsified in IFA. Twelve days after the boost mice were exsanguinated and the sera tested for Vi antibodies by ELISA. Specific antibody levels are expressed as percentage of a standard anti-Vi serum.

Figure 15:
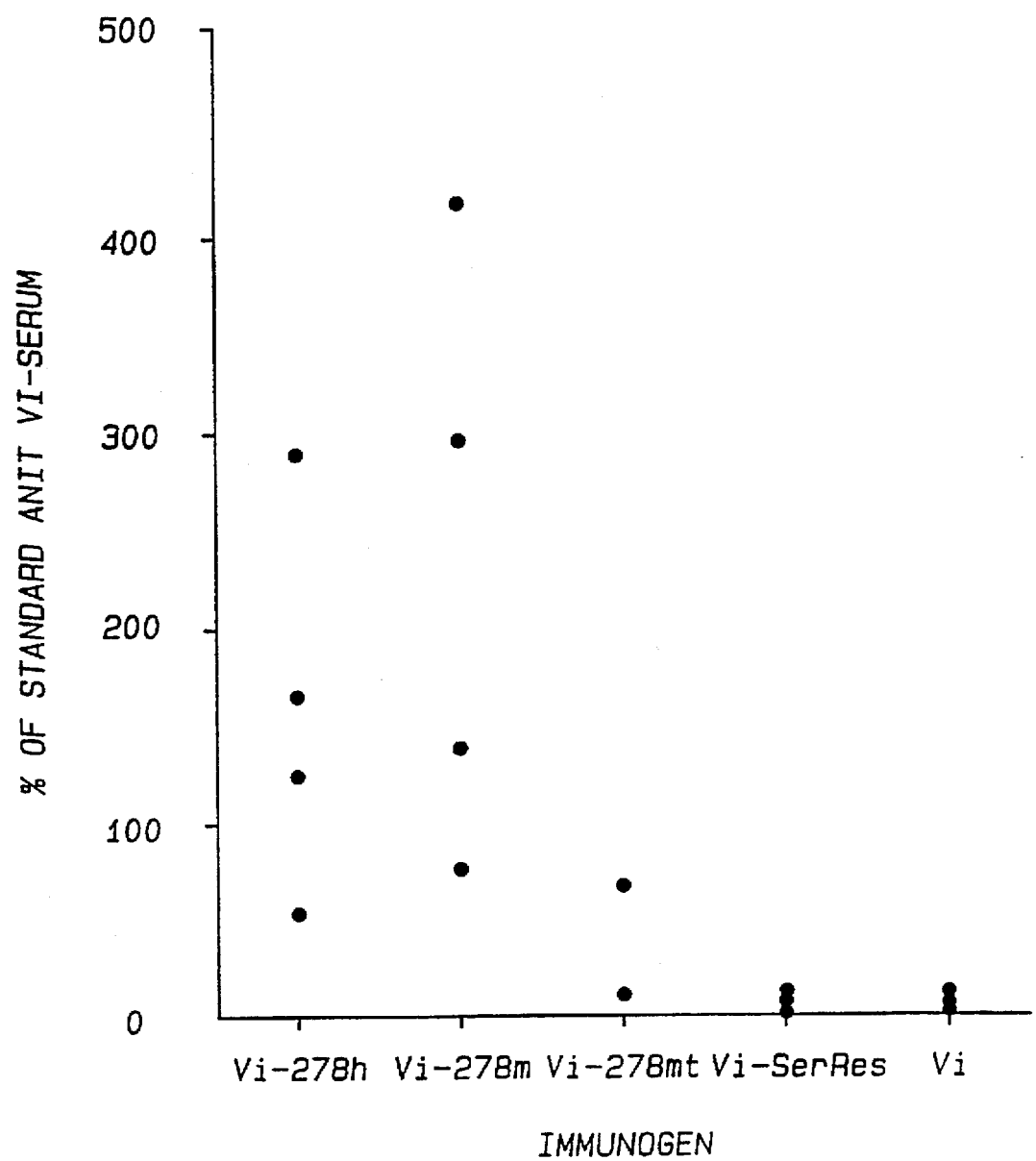
FIG. 15 illustrates the immunogenicity of Vi and conjugates Vi-278h, Vi-278m, Vi-278mt and Vi-SerRes in mice.

FIG. 15 clearly shows that a self epitope, as represented by the mouse 278m homolog, can enhance the immune response to the T-ind antigen Vi injected in BALB/c mice. The mycobacterial 278 epitope did not show any helper effect in BALB/c mice but was the only examined peptide functioning as T cell carrier in NOD as well as in NON.NOD mice (FIG. 12).

Example 5

5.1. Ability of peptide 278h to function as T cell carrier for D isomers of synthetic random branched polypeptides. Synthetic polymers composed of D isomers of amino acids are known to belong to the group of T-ind antigens. In order to find out if hsp65 derived peptides can function as T cell carrier also for this group of antigens, we examined the immune response in mice to conjugates of hsp65 peptides 278h or 348h and the synthetic polypeptide poly(Phe,Glu)-poly(Pro)-poly(Lys) (FEPK) in BALB/c mice. Three BALB/c mice were immunized sc with the polypeptide FEPK alone or conjugated to peptide 278h or 348h emulsified in IFA. Ten days after a boost with the same antigen preparation serum samples of individual mice were taken and examined for FEPK specific antibodies by a modified ELISA procedure. Plates were covered with 2.5 µg FEPK and incubated overnight at 4° C. The remaining procedure was performed as described in Material and Methods. The results are expressed as Optical density 405 ($OD_{405}$).

Figure 16:
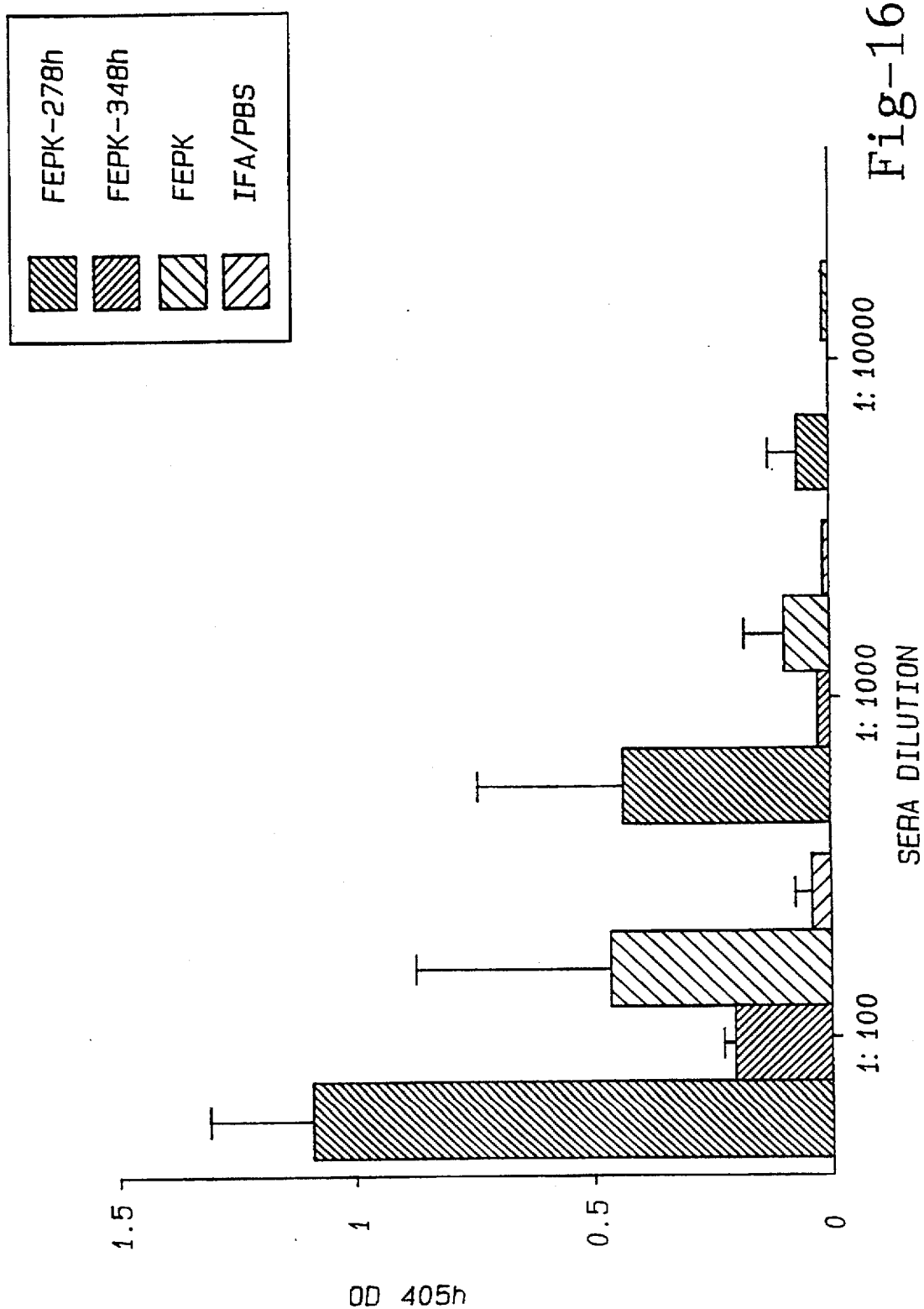
FIG. 16 illustrates the IgG1 immune response obtained in mice after immunization with polypeptide FEPK alone or conjugated with peptides 278h and 348h.

Comparing the IgG1 immune response elicited by the polypeptide alone with that induced by the polypeptide conjugated to peptide 278h demonstrate a superior immunogenicity of the conjugate. The control peptide 348h did not show any helper effect consistent with the results obtained by conjugating this peptide to the polysaccharide Vi (FIG. 16). Peptide 278h therefore can function as a T cell carrier not only for T cell independent sugar antigens but also for synthetic polypeptides composed of amino acids.

The above experiments offer evidence that the Vi-peptide conjugates of the invention are able to engage a T lymphocyte helper effect resulting in an immune response characteristic for T-dependent antigens. This evidence may be summarized as follows:

(i) The immunogenicity of Vi was increased when presented as a conjugate coupled to specific peptide candidates; this effect may not be dependent on covalent binding, since simple mixing of the two components resulted in a similar immune response.

(ii) The immunogenicity of the Vi component of the conjugate might be related to the identity of the peptide coupled to the polysaccharide. The peptides according to the invention Pep II and Pep278h enhanced the immunogenicity of Vi, while control peptides 348h, 277(S) and CRP 77–83 failed to induce a serum anti-Vi response.

(iii) Reinjection of Vi-peptide conjugates induced an increase in the level of anti-Vi antibody (booster effect).

(iv) Anti-Vi antibodies induced by vi-peptide conjugates seem to be of higher antigen-specificity than elicited by Vi alone, and are mainly presented by the IgG isotype.

(v) "Peptide priming", induced by peptide II, resulted in an enhanced serum anti-Vi antibody response to initial immunization with the corresponding Vi-peptide conjugate.

(vi) Both antigen administration via the sc route and the use of IFA seem to be necessary for inducing an anti-Vi immune response characteristic of T-dependent antigens.

All of the above results using human Pep278h have been repeated using the mouse variant Pep278m sequence, that differs from the human Pep278h in a substitution of A for T at position 471. Despite the fact that Pep278m is a self epitope for mice, it functioned as a T cell carrier in augmenting the immunogenicity of Vi. Therefore, mice respond to both mouse and human sequences which are self and nearly-self, indicating that humans will respond to the human sequence in the same way that mice respond to the mouse sequence.

All this shows that the Vi component of the polysaccharide-peptide conjugate has been converted from a thymic-independent to a thymic-dependent immunogen.

It is not obvious that peptides derived from human hsp65 can be used to enhance immunogenicity of poorly immunogenic antigen molecules, first because as a self protein human hsp65 is not considered to be immunogenic in humans, and second because it was previously shown that peptides from the human sequence, such as the Pep278, had no effect on inducing tolerance/down-regulation of autoimmune responses (WO 90/10449).

REFERENCES

Avery, O. T. and Goebel, W. F., J. Exp. Med. 59.:533–550 (1929).
Barrios, C., et al., Eur. J. Immunol..22:1365–1372 (1992).
Brett, S. J. et al., Eur. J. Immunol. 19:1303–1310 (1989).
Cohen, I. R. and Young D. B., Immunol. Today 12:105–110 (1991).
Cox et al., Eur. J. Immunol. 18:2015–2019 (1988).
Elias, D. et al., Proc. Natl. Acad. Sci. USA 87:1576–1580 (1990).
Elias, D. et al., Proc. Natl. Acad. Sci USA 89:3088–3091 (1991).
Lamb, J. R. et al., EMBO Journal 6:1245–1249 (1987).
Lussow, A. R. et al., Immunol. Letters 25:255–263 (1990).
Lussow, A. R. et al., Eur. J. Immunol. 21:2297–2302 (1991)
Merrifield, R. B., J. Am. Chem. Soc. 85:2149–2154 (1963).
Munk, M. E. et al., Eur. J. Immunol. 18:1835–1838 (1988).
Munk, M. E. et al., J. Immunol. 193:2844–2849 (1989).
Pearson, C. M., Arthritis Rheum. 7:80–86 (1964).
Szu, S. C. et al., Infect. Immun. 57:3823–3827 (1989).
Verbon, A. et al., Clin. Exp. Immun. 86:6–11 (1991).
Young, D. et al., Proc. Natl. Acad. Sci. USA 85:4267–4270 (1988).

We claim:

1. A conjugate comprising a poorly immunogenic antigen covalently attached to a synthetic peptide carrier constituting a T cell epitope of hsp65 in which said synthetic peptide carrier is selected from the group of peptides consisting of
 (a) NEDQKIGIEIIKRTLKI (Pep278h) (SEQ ID NO: 1),
 (b) NEDQKIGIEIIKRALKI (Pep278m) (SEQ ID NO:2),
 (c) EGDEATGANIVKVALEA (Pep278mt) (SEQ ID NO:3),
 (d) VLGGGSALLRSI (Pep II) (SEQ ID NO:4), and
 (e) an analog of Pep278h (SEQ ID NO: 1):

$$\overset{458}{\text{N E D Q K I G I E I I K R T L K I}}\overset{474}{}$$

that has at least 70 % of the electric and hydrophilicity/hydrophobicity characteristic of human hsp65 from position 458 to position 474, said peptide or analog being capable of increasing substantially the immunogenicity of the poorly immunogenic antigen when the conjugate is administered in vivo.

2. The conjugate according to claim 1 wherein the synthetic peptide is an analog of Pep278h (SEQ ID NO: 1):

$$\overset{458}{\text{N E D Q K I G I E I I K R T L K I}}\overset{474}{}$$

in which the residue $E^{459}$ is either E or D; the residue $D^{460}$ is either D or E; the residue $K^{462}$ is either K or R or ornithine (Orn); the residue $I^{463}$ is either I or L, V, M, F, norleucine (Nle) or norvaline (Nva); the residue $I^{465}$ residue is either I or L, V, M, F, Nle or Nva; the residue $E^{466}$ is either E or D; the residue $I^{467}$ is either I or L, V, M, F, Nle or Nva; the residue $I^{468}$ is either I or L, V, M, F, Nle or Nva; the residue $K^{469}$ is either K or R or Orn; the residue $R^{470}$ is either R, K or Orn; the residue $L^{472}$ in either L or I, V, M, F, Nle or Nva; the residue $K^{473}$ is either K or R or Orn; and the residue $I^{474}$ is either I or L, V, M, F, Nle or Nva.

3. The conjugate according to claim 1 wherein the poorly immunogenic antigen is a peptide, a protein or a polysaccharide.

4. The conjugate according to claim 3 wherein the poorly immunogenic peptide is derived from HIV virus or from malaria antigen.

5. The conjugate according to claim 3 wherein the poorly immunogenic polysaccharide is a bacterial polysaccharide.

6. The conjugate according to claim 1 wherein the synthetic peptide carrier is Pep278h (SEQ ID NO: 1).

7. The conjugate according to claim 1 wherein the synthetic peptide carrier, is Pep278m (SEQ ID NO:2).

8. A conjugate according to claim 1 wherein the synthetic peptide carrier is Pep278mt (SEQ ID NO:3).

9. The conjugate according to claim 1 wherein the synthetic peptide carrier is Pep II (SEQ ID NO:4).

10. The conjugate according to claim 1 wherein the synthetic peptide carrier or analog is directly covalently attached to the poorly immunogenic antigen molecule.

11. The conjugate according to claim 10 wherein the poorly immunogenic antigen molecule is a bacterial polysaccharide.

12. The conjugate according to claim 11 wherein the bacterial polysaccharide is the capsular polysaccharide (CPS) Vi of *Salmonella typhi*.

13. The conjugate according to claim 1 wherein the synthetic peptide carrier or analog is covalently attached to the poorly immunogenic antigenic molecule through a spacer, selected from —O—R—CO—, —NH—R—CO—, —NH—R—NH—, —O—R—NH— or —NH—R—CH$_2$—, in which R is a saturated or unsaturated hydrocarbon chain optionally substituted and/or interrupted by one or more aromatic radicals or by heteroatoms selected from N, O or S.

14. The conjugate according to claim 13 wherein R is an aliphatic hydrocarbon chain containing 3–16 carbon atoms.

15. The conjugate according to claim 14 wherein R is the residue of ε-aminocaproic acid.

16. The conjugate according to claim 15 of the formula

CO—NH—AC—CO—NH-Pep-COOH in which Ac is acetyl, AC is the residue of ε-aminocaproic acid, Pep is the residue of the peptide carrier Pep278h or Pep II and the saccharide residue represents a repeating unit of the Vi capsular polysaccharide of *Salmonella typhi*.

17. The conjugate according to claim 1 which is able to produce a T lymphocyte helper effect resulting in an immune response characteristic for T-dependent antigens.

18. The conjugate according to claim 16 which induces antibodies mainly of the IgG isotype.

19. A vaccine comprising a conjugate as claimed in claim 1, 10 or 13.

20. The vaccine according to claim 19 which contains an adjuvant.

21. A method for enhancing the immunogenicity of a poorly immunogenic antigen molecule which comprises linking it to a synthetic peptide carrier constituting a T cell epitope of hsp65 in which said synthetic peptide carrier is selected from the group of peptides consisting of
 (a) NEDQKIGIEIIKRTLKI (Pep278h) (SEQ ID NO: 1),
 (b) NEDQKIGIEIIKRALKI (Pep278m) (SEQ ID NO:2),
 (c) EGDEATGANIVKVALEA (Pep278mt) (SEQ ID NO:3), (d) VLGGGSALLRSI (Pep II) (SEQ ID NO:4), and
(e) an analog of Pep278h (SEQ ID NO: 1):

$$\overset{458}{\text{N E D Q K I G I E I I K R T L K I,}}\overset{474}{}$$

that has at least 70% of the electric and hydrophilicity/hydrophobicity characteristic of human hsp65 from position 458 to position 474, said peptide or analog being capable of increasing substantially the immunogenicity of the poorly immunogenic antigen when the conjugate is administered in vivo.

22. The method according to claim 21 in which the synthetic peptide carrier is an analog of Pep278h (SEQ. ID NO: 1) in which the residue $E^{459}$ is either E or D; the residue $D^{460}$ is either D or E; the residue $K^{462}$ is either K or R or ornithine (Orn); the residue $I^{463}$ is either I or L, V, M, F, norleucine (Nle) or norvaline (Nva); the residue $I^{465}$ residue is either I or L, V, M, F, Nle or Nva; the residue $E^{466}$ is either E or D; the residue $I^{467}$ is either I or L, V, M, F, Nle or Nva; the residue $I^{468}$ is either I or L, V, M, F, Nle or Nva; the residue $K^{469}$ is either K or R or Orn; the residue $R^{470}$ is either R, K or Orn; the residue $L^{472}$ in either L or I, V, M, F, Nle or Nva; the residue $K^{473}$ is either K or R or Orn; and the residue $I^{474}$ is either I or L, V, M. F, Nle or Nva.

23. The method according to claim 21 in which the poorly immunogenic antigen molecule is a peptide, a protein or a polysaccharide.

24. The method according to claim 21 in which the poorly immunogenic antigen molecule is a bacterial polysaccharide.

25. A method for immunization of a mammalian host which comprises administering to said host an effective amount of a conjugate of claim 1, 10 or 13.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) NAME/KEY: Peptide
        ( B ) LOCATION: 1..17
        ( D ) OTHER INFORMATION: /label=Pep278h
            / note="Corresponds to positions 458-474 of the human hsp65 molecule."

(xi) SEQUENCE DESCRIPTION: SEQ ID NO:1:

```
Asn Glu Asp Gln Lys Ile Gly Ile Glu Ile Ile Lys Arg Thr Leu Lys
1               5                   10                  15

Ile
```

(2) INFORMATION FOR SEQ ID NO:2:

(i) SEQUENCE CHARACTERISTICS:
    (A) LENGTH: 17 amino acids
    (B) TYPE: amino acid
    (C) STRANDEDNESS:
    (D) TOPOLOGY: unknown (ii) MOLECULE TYPE: peptide (ix) FEATURE:
    (A) NAME/KEY: Peptide
    (B) LOCATION: 1..17
    (D) OTHER INFORMATION: /label=Pep278m (xi) SEQUENCE DESCRIPTION: SEQ ID NO:2:

```
Asn Glu Asp Gln Lys Ile Gly Ile Glu Ile Ile Lys Arg Ala Leu Lys
1               5                   10                  15

Ile
```

(2) INFORMATION FOR SEQ ID NO:3:

(i) SEQUENCE CHARACTERISTICS:
    (A) LENGTH: 17 amino acids
    (B) TYPE: amino acid
    (C) STRANDEDNESS:
    (D) TOPOLOGY: unknown (ii) MOLECULE TYPE: peptide (ix) FEATURE:
    (A) NAME/KEY: Peptide
    (B) LOCATION: 1..17
    (D) OTHER INFORMATION: /label=Pep278mt (xi) SEQUENCE DESCRIPTION: SEQ ID NO:3:

```
Glu Gly Asp Glu Ala Thr Gly Ala Asn Ile Val Lys Val Ala Leu Glu
1               5                   10                  15

Ala
```

(2) INFORMATION FOR SEQ ID NO:4:

(i) SEQUENCE CHARACTERISTICS:
    (A) LENGTH: 12 amino acids
    (B) TYPE: amino acid
    (C) STRANDEDNESS:
    (D) TOPOLOGY: unknown (ii) MOLECULE TYPE: peptide (ix) FEATURE:
    (A) NAME/KEY: Peptide
    (B) LOCATION: 1..12
    (D) OTHER INFORMATION: /label=PepII
      / note="Corresponds to positions 437-448 of the human
      hsp65 molecule in which the two Cys moieties have been
      replaced by Ser at positions 442 and 447."

(xi) SEQUENCE DESCRIPTION: SEQ ID NO:4:

```
Val Leu Gly Gly Gly Ser Ala Leu Leu Arg Ser Ile
1               5                   10
```

( 2 ) INFORMATION FOR SEQ ID NO:5:

( i ) SEQUENCE CHARACTERISTICS:
        ( A ) LENGTH: 24 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) NAME/KEY: Peptide
        ( B ) LOCATION: 1..24
        ( D ) OTHER INFORMATION: /label=Pep277S ( x i ) SEQUENCE DESCRIPTION: SEQ ID NO:5:

```
Val Leu Gly Gly Gly Ser Ala Leu Leu Arg Ser Ile Pro Ala Leu Asp
 1               5                   10                  15

Ser Leu Thr Pro Ala Asn Glu Asp
                 20
```

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) NAME/KEY: Peptide
        ( B ) LOCATION: 1..12
        ( D ) OTHER INFORMATION: /label=348h
            / note="Corresponds to positions 449-460 of the human
              hsp65 molecule"

( x i ) SEQUENCE DESCRIPTION: SEQ ID NO:6:

```
Pro Ala Leu Asp Ser Leu Thr Pro Ala Asn Glu Asp
 1               5                   10
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: unknown ( i i ) MOLECULE TYPE: peptide ( i x ) FEATURE:
        ( A ) NAME/KEY: Peptide
        ( B ) LOCATION: 1..7
        ( D ) OTHER INFORMATION: /label=PepCRP77-83
            / note="Corresponds to positions 77-83 of the Human
              C- Reactive Protein"

( x i ) SEQUENCE DESCRIPTION: SEQ ID NO:7:

```
Val Gly Gly Ser Glu Ile Leu
 1               5
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: unknown ( i i ) MOLECULE TYPE: peptide (ix) FEATURE:
 (A) NAME/KEY: Peptide
 (B) LOCATION: 1..18
 (D) OTHER INFORMATION: /label=PepSerRes (xi) SEQUENCE DESCRIPTION: SEQ ID NO:8:

Leu Arg Gly Gly Gly Val Cys Gly Pro Ala Gly Pro Ala Gly Thr Val
1               5                   10                  15
Cys Ser